United States Patent [19]
Bonaventura et al.

[11] Patent Number: 5,998,200
[45] Date of Patent: Dec. 7, 1999

[54] ANTI-FOULING METHODS USING ENZYME COATINGS

[75] Inventors: Celia Bonaventura; Joseph Bonaventura; Irving R. Hooper, all of Beaufort, N.C.

[73] Assignee: Duke University, Durham, N.C.

[21] Appl. No.: 07/683,130

[22] Filed: Apr. 10, 1991

Related U.S. Application Data

[63] Continuation of application No. 07/464,699, Jan. 16, 1990, abandoned, which is a continuation of application No. 06/744,547, Jun. 14, 1985, abandoned.

[51] Int. Cl.⁶ ........................................ C12S 9/00
[52] U.S. Cl. .................. 435/264; 435/174; 435/180; 424/94.1; 424/94.63; 106/15.05; 422/6
[58] Field of Search ........................ 435/174, 262, 435/263, 264, 267, 261, 194, 175, 182; 422/6; 106/15.05, 18.32; 71/67; 424/405, 409, 484, 486, 78.08, 78.09, 94.1, 94.4, 94.64, 94.61–94.63, 94.65–94.67

[56] References Cited

U.S. PATENT DOCUMENTS

| | | | |
|---|---|---|---|
| 3,773,623 | 11/1973 | Hatcher et al. | 435/264 X |
| 4,055,467 | 10/1977 | Christensen et al. | 435/264 |
| 4,059,485 | 11/1977 | Tolbert et al. | 435/262 X |
| 4,090,921 | 5/1978 | Sawamura et al. | 435/288 X |
| 4,234,340 | 11/1980 | Pellico | 106/15.05 |
| 4,480,011 | 10/1984 | Durano et al. | 106/15.05 |
| 4,486,330 | 12/1984 | Yoshida et al. | 435/264 X |
| 4,540,506 | 9/1985 | Jacobsen et al. | 435/264 X |
| 4,552,813 | 11/1985 | Grams | 428/411.1 |
| 4,602,959 | 7/1986 | Kurita et al. | 106/15.05 |
| 4,610,800 | 9/1986 | Durham et al. | 435/264 X |
| 4,678,512 | 7/1987 | Grams | 106/18.32 |

OTHER PUBLICATIONS

Christie, A.O. "Control of Fouling Organisms." in: Conference Book of International Paint Marine Coatings (London, OYEZ IBC, 1979), pp. 1–4.

Abstract of JP 60028467, Feb. 13, 1985.
Abstract of JP 51000533, Jan. 6, 1976.
Abstract of JP 60078901, Apr. 5, 1985.
Wayne et al. Abstract CA:92(4):27972e, 1979.
Christie Abstract #Dialog File 44:0062363 40–05970. "Control of fouling organisms", Apr. 23, 1979.
Christie et al. Abstract CA73(9):42502c, "Ship–fouling alga Enteromorpha II", 1970.
Trevan, Immobilized Enzymes, John Wiley & Sons, New York, 1980, pp. 66–70.
Kirk–Othmer Encyclopedia of Chemical Technology, Third Edition, vol. 16, Noise Pollution to Perfumes (1981) p. 797.
Biotechnology of Marine Polysaccharides, Proceedings of the Third Annual MIT Sea Grant College Program Lecture and Seminar (No date provided) pp. 520–521.
Physiology and Biochemistry of Algae, Edited by Ralph A. Lewin, Scripps Institution of Oceanography, Univesity of California, La Jolla, California pp. 475–489 (1962).
Patent Office of Japan Patent Publication No. 63–202677 (Aug. 1988).
Republic of France Patent Application Publication No. 2 562 564 (Oct. 1985).
Foul Play Under Water (No date Provided).

*Primary Examiner*—William H. Beisner
*Attorney, Agent, or Firm*—Oblon, Spivak, McClelland, Maier & Neustadt, P.C.

[57] ABSTRACT

A method for preventing fouling of an aquatic apparatus by an aquatic organism which comprises affixing a biologically active chemical to a surface intended for use in contact with an aquatic environment containing the organism, wherein the chemical is an enzyme, repellant, chelating agent, enzyme inhibitor, or non-metallic toxicant capable of hindering the attachment of the organism to the surface while affixed to the surface, is disclosed along with improved apparatuses which are produced using the method.

14 Claims, 1 Drawing Sheet

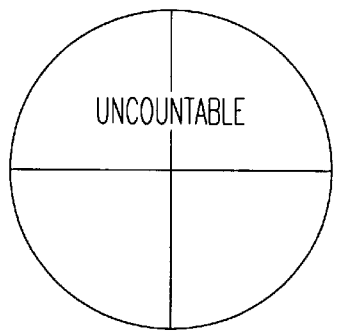 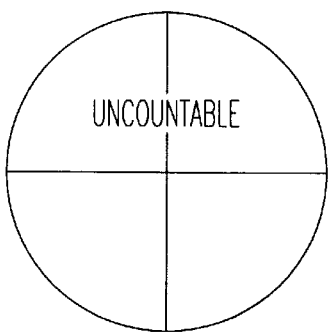 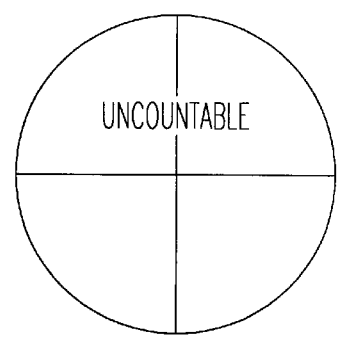
ALBUMIN TREATED – BACTERIAL DEATH AVERAGE = 30% OF INTRODUCED COLONIES
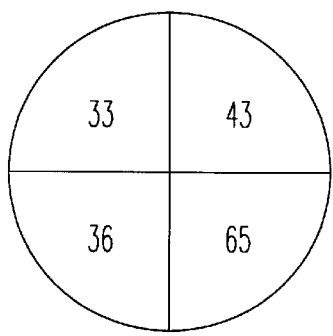 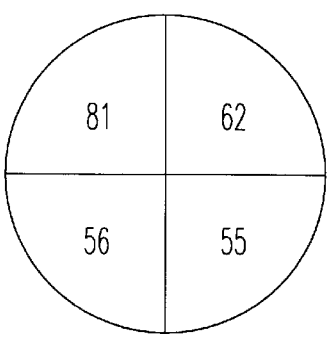 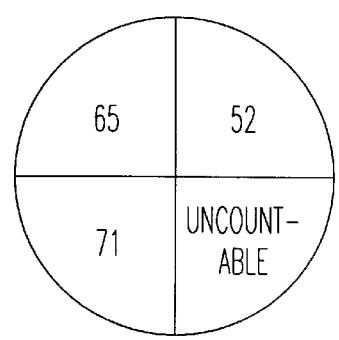
ACHROMOPEPTIDASE TREATED – BACTERIAL DEATH AVERAGE = 85% OF INTRODUCED COLONIES
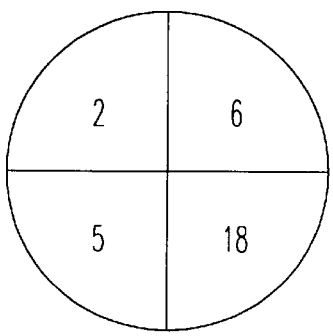 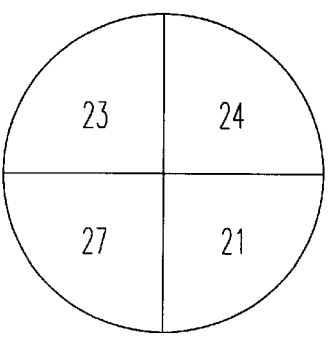 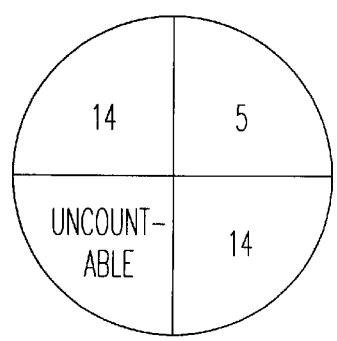

ANTI-FOULING METHODS USING ENZYME COATINGS

This application is a Continuation of application Ser. No. 07/464,699, filed on Jan. 16, 1990, now abandoned, which was a continuation application of Ser. No. 06/744,547, filed Jun. 14, 1985, abandoned.

BACKGROUND OF THE INVENTION

1. Field of the Invention

This invention relates to methods and compositions for the treatment of submerged surfaces, such as marine or other aquatic structures of ship hulls, in order to prevent fouling of the surfaces by aquatic organisms.

2. Description of the Background

It is well-known that the growth of organisms (micro- or macro-fouling matters) on the submerged parts of a structure may have detrimental effects on their operation and their corrosion rate. For example, in the techniques of oil production at sea, the fouling may accelerate the corrosion of submerged structures such as supports of drilling platforms. The weight increase resulting from the deposit of the fouling matter also results in difficulties when raising up certain submerged structures, as it is the case for the pipe-lines used to collect oil at sea; it also requires frequent operations for the maintenance of the floats of signal or meterologic buoys. On the other hand, the formation of even a very thin layer of microfouling is sufficient to reduce the transmission of light and sound and consequently to disturb the operation of certain devices such as sonar sea-marks. The fouling matter may also be a medium favorable to the proliferation of certain microorganisms responsible for the biodegradation of organic materials and of concrete. It is also known that the cooling systems for plants and power stations, either of the nuclear or of the conventional type, that are operated with sea water are also subject to severe fouling which may plug ducts and condensors. Finally, fouling by large organisms such as the balani, the serpulae and the algae, increases the roughness of the hull of ships and their drag in water, thereby resulting in an increase of fuel consumption and/or a reduction of the ship speed. These various problems and their consequences emphasize the importance of anti-fouling substances.

Besides the periodic cleaning of the surfaces or the use of paints enabling a controlled exfoliation, which are very expensive remedies, the principle of most anti-fouling action is to create a toxic zone on the surfaces to be protected. For example, chlorine is used successfully in a continuous manner in sea water ducts, but this technique is obviously unsatisfactory as far as the preservation of the natural environment is concerned.

An efficient way of combating fouling must (by prior art) comprise the maintenance of the toxic product at an efficient and homogeneous concentration and in a continuous manner on the whole surface. This is the reason why the so-called "anti-fouling" paints have taken an important place among the anti-fouling means. Thus, in order to fight against the growth of sea organisms on submerged surfaces and hulls of boats, an anti-fouling paint is generally applied as an upper layer. According to the known techniques, this anti-fouling paint contains a toxic substance which slowly reacts with sea-water to give a salt soluble in water and which is lixiviated from the paint pellicle. Among the toxic substances which are the most commonly used, there can be mentioned cuprous oxide, tin tri-n-butyl oxide, tin tri-n-butyl fluoride and tin tri-n-butyl sulfide, these compounds being biocidic agents with activity against a wide range of a sea organisms. However, the lixiviation process cannot, even in these cases, be controlled uniformly. Generally, it is much too fast immediately after a submerged structure has been put into service with, as a consequence, the initial presence, near the material to be protected, of very high concentrations of toxic matters, higher than those actually required. This results in a loss of toxic agent and in pollution of the environment and, thereafter, the presence of a lower concentration of toxic material than that necessary to obtain efficient protection, which results accordingly in the accumulation of fouling-organisms.

In order to obviate these disadvantages, a recently proposed solution of the prior art consisted of applying a surface coating containing a polymer wherein the toxic groups are chemically combined, thereby decreasing, as a general rule, the lixiviation rate of the biocidic compound in the aqueous phase and extending the effective life of the paint. These biocidic coatings generally contain organo tin compounds chemically bonded to the polymer substrate through a hydrolyzable ionic bond. They consist essentially of polyesters or polyepoxide resins containing organo-tin derivatives or metal salts, as proposed for example, in French Patent Specification Nos. 2,266,733 and 2,307,957 and U.S. Pat. Nos. 3,167,473; 3,684,752 and 3,979,354. These organometallic resins are generally obtained either by polymerization or copolymerization of organometallic unsaturated monomers, or by reaction of a suitable organometallic compound with a resin comprising carboxyl groups. These methods have been described, for example, in U.S. Pat. No. 3,016,369 and in Journal of Polymer Science vol. 32 No. 125 (1958), pages 523 to 525. However there has been no solution proposed to the problem of fouling of submerged surfaces that does not involve the release of toxic compounds, such as are now in wide use. Moreover, no solution has been proposed for replacing them with substances which cause less harm to the environment.

SUMMARY OF THE INVENTION

Accordingly, it is an object of the present invention to provide a method of preventing fouling of aquatic surfaces by organisms which does not contaminate the environment to the extent that contamination occurred using previous anti-fouling methods.

This and other objects of the invention as will hereinafter become more readily apparent have been accomplished by providing a method for preventing fouling of an aquatic apparatus by an aquatic organism which comprises affixing biologically active chemicals to a surface intended for use in contact with an aquatic environment containing said organism wherein said chemicals possess anti-fouling properties in a bound state. As will be shown, the attachment and/or growth and development of organisms on a submerged surface may be hindered by use of non-toxic coatings containing combinations of immobilized bioactive species, these being enzymes, enzyme inhibitors, repellants, chelating agents, surfactants or non-metallic toxicants. These chemicals are differentiated from the active ingredients of common anti-fouling coatings in that they are biologically active without being released and are not metallic toxicants. Although many enzymes that may find use in this invention contain metals, they are not metallic toxicants and have little structural relation to the copper and tin compounds used in common anti-fouling coatings.

BRIEF DESCRIPTION OF THE DRAWING

The FIGURE shows the inhibition of *S. epidermidis* growth of rinsed but unsterilized silicones after immobilization of bioactive materials. The average number of introduced CFUs per quadrant was 82. The numbers represent the total CFUs per quadrant after allowing the bacteria to grow.

DESCRIPTION OF THE PREFERRED EMBODIMENTS

Generally the prior art has made use of coatings containing toxic materials, preferentially metals, capable of killing aquatic organisms in slow-release formulations, in an attempt to prevent organisms from growing on coated submerged surfaces. A common feature is the need for the toxic material to be released from the surface and ingested by the organism. Release, however, is a continuous process, so that environmental pollution occurs and the toxic material must be periodically replaced.

The approach of the present invention is to use less toxic or nontoxic materials which interfere with the attachment process or with growth, metamorphosis proliferation, or development of aquatic organisms while still attached to the surface rather than to use materials which are toxic to organisms in general. The invention involves the confinement of a biologically active chemical on or within an inert matrix which is applied to a surface intended for contact with an aquatic environment. Alternatively, the surface can be functionalized and the active chemicals can be covalently bonded (or otherwise chemically affixed) directly to the surface. The chemicals used possess anti-fouling properties in their bound state, being typically enzymes, enzyme inhibitors, repellants, surfactants, chelating agents, or non-metallic toxicants capable of hindering the attachment, growth or development of an organism on the surface being protected. Since the active chemicals are immobilized on or in the surface being protected, their release to the environment is minimal. However, if release does occur, as by weathering or biological attack, the materials of the invention are not biologically accumulated by organisms and accordingly do not create a source of environmental pollution harmful to higher organisms. In that these active materials are not principally heavy metals or other general toxicants, they will cause much less contamination of the environment than their counterparts that are now in common use.

Table I lists a number of species of the major groups of plants, and of the major animal groups, which constitute the fouling community.

TABLE I

Species diversity of the fouling community (Woods Hole Oceanographic Institute 1952).

| Organism | Number of Reported Fouling Species |
|---|---|
| Plants | |
| Bacteria | 37 |
| Fungi | 14 |
| Algae | 563 |
| Animals | |
| Protozoa | 99 |
| Porifera | 33 |
| Coelenterata | 286 |
| Platyhelminthes | 12 |
| Nemertea | 11 |
| Rotifera | 5 |
| Bryozoa | 139 |
| Brachiopoda | 1 |

TABLE I-continued

Species diversity of the fouling community (Woods Hole Oceanographic Institute 1952).

| Organism | Number of Reported Fouling Species |
|---|---|
| Annelida | 108 |
| Arthropoda | 292 |
| Mollusca | 212 |
| Echinodermata | 19 |
| Chordata | 127 |

It is evident that the development of an anti-fouling agent which could eliminate only, for example, barnacles would be solving only part of the fouling problem. However, there is no need to develop a specific immobilized chemical, or a specific combination of immobilized chemicals, for each member of the fouling community. General rules developed by the inventors exist to guide in the production of fully active anti-fouling compositions.

First, it will be noted that not all members of the fouling community play an equal role in the development of the community. Studies on the temporal development of a fouling community have revealed that bacteria are usually the first organisms to colonize a submerged surface. Attached bacteria produce a secondary extracellular polymeric adhesive, and eventually the surface of the substratum becomes coated with bacteria embedded within this extracellular matrix (collectively referred to as a bacterial film). The rate of subsequent colonization by other microorganisms, and by marine invertebrate larvae, is often dependent upon the initial formation of a bacterial film. Consequently, the development of immobilized chemicals which restrict or eliminate the process of bacterial film formation will have a disproportionately large anti-fouling effect.

Second, it is also relevant to the practice of this invention and the development of non-toxic anti-fouling coatings that a small number of Proteins and carbohydrates constitute the important structural elements of the cell wall of plants and the integument of animals. Collagen, cellulose, and chitin are probably the three most abundant structural polymers in the plant and animal kingdoms. Chitin, for example, is an important constitutent of the shell matrix of the inarticulate Brachipoda, the exoskeleton of the Ectoprocta (e.g. Bryozoa), the walls of sponge gemmules (the dispersal stage of the sponge life cycle), the perisarc (the outer layer of the integument) of hydrozoan coelenterates, the cell wall of fungi, and the cuticle of all arthropods. These organisms combined a account for approximately 40% of the total reported number of fouling species shown in Table I. The integument of most fouling organisms is the principal organ of permanent post-metamorphic attachment and adhesion. Interference with the synthesis of an important biochemical constituent of the cell wall or integument, or any degradation of such structural elements or interference with the enzymatic processes involved in adhesion would therefore exert a strong anti-fouling action. As shown in the following examples, substratum attachment of bryozoans and crustaceans (adult barnacles) is significantly inhibited by a coating containing immobilized chitinase. In a similar manner other immobilized enzymes and non-metallic antimicrobials in coatings show activity against the settlement of specific organisms.

Biologically active chemicals capable of being used in the practice of the present invention include enzymes, enzyme inhibitors, repellants, chelating agents, surfactants and non-metallic toxicants.

In selecting these active agents, those which are selected for a particular application will naturally vary with the type of surface being protected, the environment in which it is found, and the organism against which protection is being sought. The general principle underlying the choice of the bioactive material to be immobilized is that the abundance of a particular type of bioactive compound should be proportional to the probable frequency of surface contact with the target organism against which the compound has antifouling efficacy. As an example, a short-term protection against settling organisms in a marine environment can focus on deterring the formation of films that are deposited by the settlement and growth of marine algae and bacteria. In this case, the bioactive materials to be incorporated on the surface can be distributed equally between a bactericide and an algaecide. The bacterial and algae film production is believed by some experts in the field to be a prerequisite for most macrofouling. Macrofouling refers to the attachment of organisms larger than unicellular organisms to an aquatic surface. According to this view, very little or no enzyme or other chemical antifoulant capable of disrupting the attachment process of macrofouling organisms would need to be included. However, in a region that is heavily populated with barnacle larvae, enzymes or other chemical artifoulants that specifically retard the settlement of the barnacle larva would be more important and should be incorporated on a surface, preferably in larger proportion. Accordingly, a preferred composition for any given environment will include one or many active compounds present in proportions that range from 5 to 100% of the total active compounds for any individual compound.

Particularly preferred are methods of affixing active compounds to surfaces which result in a monolayer of active compounds on the surface. For example, a protease or other enzyme having a molecular weight of approximately 50,000 daltons would give a monolayer when spaced on a surface with a distance of approximately 40 angstroms between the centers of adjacent molecules. This spacing assumes a Stokes radius of approximately 20 angstroms. However, it is not essential that a complete monolayer be present and suitable activity can be maintained while spacing bioactive compounds at greater distances. However, a spacing of no more than 1,000 angstroms and more preferably no more than 100 angstroms is preferred in order to insure that a biologically active chemical is available for reaction with a fouling organism at the point of initial contact.

The method of the present invention and the surfaces produced according to the method are useful in all types of aquatic environments, including sea-water, estuary, and fresh water environments. In addition to natural environments (i.e., those which are in free contact with and freely exchange material with other parts of the biosphere without human intervention), the term "aquatic environments" as used herein also includes cooling towers, fresh and salt water piping systems, desalination and other filtration systems containing membrane "surfaces" subject to protection, and other aquatic environments which rely upon the intervention of human beings for their creation and maintenance. As used herein, the term "natural environment" includes ponds, lakes, dredged channels and harbors, and other bodies of water which were initially produced by the action of human beings but which do not rely upon human intervention for the supply of water into and out of such environments.

While many fouling organisms such as barnacles and algae are well known to the general public, those skilled in the art will recognize that the term fouling organism as used herein refers to any living organism which is capable of attaching to a surface in an aquatic environment. The term microfouling is used to denote the attachment of unicellular organisms, such as bacteria and algae, to the submerged surface. These microfouling organisms can, in some cases, secrete chemical signals which attract further organism to the surface, thereby increasing the rate of fouling. Macrofoulers, such as barnacles, become attached to the surface after the formation of the initial microfouling layer. It is held by some experts in the field that since microfouling generally occurs before the macrofouling, any process which interferes with the attachment of micro organisms to aquatic surfaces would decrease the total amount of fouling which takes place. Thus, an active ingredient capable of preventing the attachment of barnacles operates at the end of the fouling chain while an active agent which operates to prevent the attachment of unicellular organisms such as bacteria operates at the beginning of the fouling chain. Accordingly, agents which prevent microfouling may have some inhibitory effect against settlement of all types of fouling.

Immobilized biologically active chemicals of choice in providing anti-fouling protection in coatings of the invention can be selected on the basis of their known toxicity, their ability to degrade or interfere with formation of an organism's substratum adhesive and/or its adverse effects on cell or body walls.

Table II lists the known chemical characteristics of the adhesives produced by fouling organisms. "Pre-settlement" adhesives enable the organism to maintain contact with the substratum during an exploratory period which precedes permanent attachment. Attachment at this time is reversible. "Settlement" and "post-metamorphic" adhesives serve to permanently affix the organism to the substratum.

TABLE II

Substratum adhesives of fouling species.

| Organism | Presettlement Adhesive | Settlement/Postsettlement Adhesive | Reference |
| --- | --- | --- | --- |
| Bacteria (Pseudomonas) | protein & polysaccharide? | protein and polysaccharide | Fletcher 1980xx xxxx |
| Coelenterata (Hydrozoa) | nematocysts | mucopolysaccharide? | |
| Algae (Entermopha) | — | glyco-protein | Callow and Evans 1977 |
| Bryozoa (Cheilostomat | acidic mucopolysaccharide | protein and sulfonated acidic mucpolysaccharide | Loeb and Walker 1977 Reed 1978 |
| Mollusca | nucuous threads | quinone cross-linked protein | Cranfield 1975 |
| Arthropoda | secretion from cyprid antennule? | cyprid: alkaline protein which may be cross-linked by phenols; Adult: acidic protein which may be cross-linked by phenols and/or S-S or S41 groups | see text |

TABLE II-continued

Substratum adhesives of fouling species.

| Organism | Presettlement Adhesive | Settlement/Postsettlement Adhesive | Reference |
|---|---|---|---|
| Annelida (Spirorbinae) | mucuous threads has a high calcium content | sulfonated polysaccharide which Nott 1973 | Hedley 1956 |
| Chordata (Tunicata) | — | protein with many S-S and S-H groups, and a sulfonated acidic mucopolysaccharide | Lane 1973 |

Table II indicates that the permanent adhesives are predominantly proteinaceous or consist of mixtures of proteins and carbohydrates. Very little is understood about the identity of the principal molecular elements of any adhesive or the molecular mechanisms responsible for hardening of the adhesive. Protein cross-linking by phenolic groups, or by sulfhydryl groups of the constituent amino acids, have been suggested as the basis of the hardening of barnacle cement. Nevertheless, it is not necessary to know these theoretical matters in order to practice the invention since bioactive compounds can be tested simply on the basis of their ability to hinder attachment of fouling organisms while affixed, a characteristic that can be determined by simple observation.

Bioactive compounds of choice in regard to the practice of this invention are listed in Table III.

TABLE III

BIOACTIVE COMPOUNDS OF CHOICE FOR PREPARATION OF ANTIFOULING COATINGS OF REDUCED TOXICITY

| ENZYMES | Examples for Description |
|---|---|
| Serine Proteases | |
| Type I | Trypsin, Chymotrypsin |
| Tppe II | Subtilisin |
| Sulfhydryl Proteases | Papain, Chromopapain |
| Metalloproteases | Carboxypeptidase A, Carboxypeptidase B, Thermolysin |

Other proteases such as Calcium-Activated Proteases, ATP-Activated Proteases, Exopeptidases (Aminopeptidases and Carboxypeptidases) and Endopeptidases. Enzymes with the potential for degrading the polysaccharide component of adhesives or cell wall components, specific examples being α-amylase, β-amylase, β-glucosidase, glucosidase, glycosidase, cellulase, pectinase, collagenase, hyaluonidase, β-glucuronidase, lysozyme, and achromopeptides.

ENZYME INHIBITORS

Polyphenol oxidase inhibitors which will block crosslinking of cement substances and attachment, an example being kojic acid; chitin synthetase inhibitors, such as diflubenzuron and dimilin; glucosyl transferase inhibitors such as mutastein, ribcitrin 1-deoxy nojirimkycin acarbose, etc., to inhibit formation of polysaccharide adhesives.

| | |
|---|---|
| REPELLANTS | Cell homogenates or purified repellants from algae, corals or tunicates having little or no fouling of their external surfaces. |
| CHELATORS | Nitriloacetic acid, mercaptoacetic acid, hydroxamic acid, and catachols. |
| SURFACTANTS | Cationic, anionic and non-ionic surfactants such as dipalmitoyl phosphatidyl choline, aralkkyl sulfonates and sucrose esters, respectively |
| NON-METALLIC TOXICANTS gramicidin, biocides such as chlor- | Antiobiotics such as polymixin B and |
| | hexidine, 8-hydroxyquinoline and related compopunds, phenols, arsinilic acid and derivatives thereof, quaternary ammoniuim biocides, and other materiais knm to inhibit growth or attachuent, examples being tannic acid, benzoic acid, phenylthio urea, thiosalicylic acid and long chain alcohols. |

A class of active ingredients useful in the practice of the present invention and itemized in Table III includes enzymes which are capable of hindering the attachment of either microfoulers or macrofoulers. Bacteria, for example, are known to attach to surfaces by the excretion of various polysaccharides which adhere to the surface in question. Accordingly, enzymes capable of disrupting polysaccharide bonds (such as galactosidase and galactouronidase) will prevent the attachment of such microorganism when the enzymes are affixed to the surface being protected as described herein.

Enzymes may also be selected which interfere with the attachment of macrofoulers. Since macrofoulers typically go through a series of life stages during and after the initial attachment process, a variety of enzymes can be used to retard or otherwise hinder the attachment of these organisms. For purposes of illustration, several examples of immobilized chemicals which may use to counter attachment of the barnacle at various stages of its life are discussed later in this specification, although it will be recognized by those skilled in the art that the same enzymes discussed for use with the barnacle can also be used to hinder the attachment of other organisms.

Enzymes capable of degrading polysaccharides have been chosen for their potential to break down a polysaccharide component of an adhesive and/or their ability to degrade important structural polysaccharides. As mentioned, the enzymes and enzyme inhibitors of choice are those that can prevent or interfere with the attachment process or the subsequent growth, metamorphosis or replication of the fouling organisms in question. As a general feature, these enzymes of choice will be those with high stability that are not degraded or transformed into non-active materials by virtue of their anti-fouling action. Examples are those cited in Table III.

The enzymes β-amylase, β-glucosidase, and glycosidase belong to the group of enzymes that can degrade polysaccharides. Pectinase and cellulase are enzymes which break down pectin and cellulose, respectively, two ubiquitous structural polymers of the plant cell wall and cell wall connective tissue matrix. Lysozyme and achromopeptidase can also break cell walls, the latter having an exceptional range of activity against microorganisms. Hyaluronic acid and collagen have analogous structural roles in animals and are degraded by hyaluronidase and collagenase, respectively. β-Glucuronidase will also break down hyaluronic acid. Proteinaceous materials involved in fouling the surfaces are subject to disruption by proteases. Families of proteolytic enzymes are well known, as reviewed in Neurath, *Science* 224, 350–357, 1984. Candidates for use in non-toxic anti-fouling coatings can be drawn from these families, there being trypsin and subtilisn as an example of serine proteases I and II, papain as examples of sulfhydryl proteases, pepsin as an example of acid proteases, carboxypeptidase A and B and thermolysin as examples of metalloproteases I and II. Other protease families of relevance are the aminopeptidases, the collagenases and the calcium and ATP-activiated proteases, each with numerous examples.

Another type of agent useful in preventing fouling, particularly macrofouling, are the repellants of the macrofouling organisms. As discussed above, chemical signals are generally present which attract macrofoulers to the surfaces. There also exist biologically active compounds which repell rather than attract such organisms. Such repellants include molecules that are customarily associated with some inimicable material formed by a predator (or other non-compatible organism) of the macrofouling organism. An example is the material customarily excreted by starfish that causes such prey organism as scallops to immediately react to the material and try to escape therefrom. When affixed to a surface as described herein, the repellant would not freely diffuse but would act to elicit the escape response when the organism contacted the surface being protected. An example of this would be a purified chemical repellant or an impure suspension containing the active chemical repellant that is obtained by grinding and partially fractionating a coral or algae preparation. The repellants of choice are those natural products used by corals, seaweeds and other aquatic organisms to avoid fouling of their surfaces. In addition to natural products that can act as repellants, the surface protection brought about by affixing a surfactant can be considered as a repellant effect. The surfactant-treated surface is repellant in that it is unlike any found in natural waters. As set forth in the examples which follow, such surfactant-treated surfaces are repellant to some organisms.

Since surfactants are not regarded as repellants in all senses of the word, they are considered as another class of bioactive compounds having utility in this invention. As set forth in the examples which follow, a surfactant can have an inhibitory effect on attachment of organisms to a surface even when immobilized on or within a protective coating. Specific examples of immobilized surfactants, as listed in Table III, include quaternary ammonium compounds. Other examples are set forth in the Kirk-Othmer *Encyclopedia of Chemical Technology*, Vol. 22, pages 332–432, John Wiley & Sons, New York, 1983.

Tannic acid is a representative compound of the tannins, a family of compounds secreted by certain species of marine brown algae (e.g. Sargassum), which appear to restrict bacterial colonization of the frond surface (Sieburth and Conover (1965) Nature 208 52). This is exemplary of the class of compounds, useful in non-toxic anti-fouling coatings, that act by interference with enzymatic reactions necessary for attachment of macro- or micro-organisms. Candidate compounds in this category include kojic acid and similar inhibitors of polyphenol oxidase. These inhibitors will interfere with the cross-linking of cement-forming materials. of similar value are glucosyl transferase inhibitors which will prevent the formation of polysaccharide adhesives used in adhesion, mutastein, ribocitrin, 1-deoxynojirimycin, acarbose, and N-methyldeoxynojirimycin being exemplary of these. Relevant observations are that polyurethane paints containing either tannic acid, benzoic acid, or acrylamide have been reported to resist bacterial colonization and the subsequent development of barnacle populations. Whether these agents were slowly released or immobilized was not clear. In solution, a-amylase, trypsin and (bacterial) pronase have been shown to weaken the attachment of the zoospores of the fouling alga *Enteromorpha intestinalis*, and phenylthiourea and thiosalicylic acid are known to inhibit algal growth as are certain quaternary ammonium compounds. However, these compounds were not affixed to the surfaces being protected but were free in solution.

Success in substratum (surface) attachment of adult barnacles is dependent upon the unimpaired operation of various physiological processes critical to normal shell growth. A critical part of the process of barnacle shell growth is the formation of the layer of cuticle which forms the base of the shell. The set of chemicals that can interfere with this process may be useful in preventing the growth and development of barnacles. The polysaccharide chitin, an important structural constituent of cuticle, is degraded by the enzyme chitinase. Thus, the anti-fouling action of chitinase in adult barnacles occurs as a result of its interference with the formation and/or maintenance of the basal cuticle. As set forth in the examples which follow, the anti-fouling capabilities of chitinase affixed to an aquatic surface have been demonstrated.

A different mechanism is important for the attachment of barnacle larvae to surfaces, and a different set of active ingredients is useful for the prevention of larval attachment. The members of this set of chemicals overlap with the set identified above, so that a single chemical antifoulant may act on both larval settlement and on later stages of growth and development. In a purely mechanical sense, success in larval substratum attachment is dependent only upon the extrusion of a permanent adhesive material onto the substratum. Thus, if the substratum (protected surface) were impregnated only with chitinase, protection would occur only after metamorphosis of the larva to the juvenile stage. However, other proteolytic enzymes such as papaya protease, Sreptomyces protease and achromopeptidase have inhibitory effects on barnacle larva settlement.

It should be emphasized that qualitative and quantitative variation in sensitivity to immobilized chemicals between larval and adult barnacles (or the corresponding stages of other organisms) does not affect the utility of this invention. It is not esential that an anti-fouling agent act on the larva in order to be effective. For example, the traditional copper-containing anti-fouling paints allow larval forms to settle and exhibit their dramatic anti-fouling effect by killing the organism at a later stage.

Another type of biologically active chemical useful in carrying out the present invention is a chelating agent. Such compounds are effective against particular organisms which require the presence of a metal ion (generally as a cofactor of an enzyme) in order to complete the attachment process for that organism. For example, copper ions are essential for the correct operation of an exoenzyme that causes the barnacle prepolymer extrudate to cure. Accordingly, a chelating agent capable of removing copper ions from the environment directly adjacent to the surface being protected will hinder attachment of barnacles. Other types of chelating agents suitable for preventing the attachment of aquatic organisms include tethered chelators that enter cells and thereby disrupt metabolism. Specific examples of suitable chelating agents for carrying out this aspect of the invention include immobilized forms of such chelators as EDTA and hydroxamic acid.

Active ingredients which are effective against the initial microfouling stage also include non-metallic toxicants which are generally regarded as antimicrobial agents, often active by virtue of disrupting bacterial cell walls. Suitable types of non-metallic toxicants include those listed in Table III. Non-metallic toxicants having utility in the immobilized state in anti-fouling coatings are chemicals such as are recognized as antimicrobials (algicides, fungicides, bacteriocides and such antibiotics as maintain functionality when immobilized). Of choice among these are metallic or povidone iodine, long chain primary alcohols, phenols and phenol derivatives 8-hydroxy quinoline derivatives, quaternary ammonium compounds, alkylamine-substituted amino acids, nitrofuran derivatives and, as a specific antibiotic of choice for having documented functionality in an immobilized state, polymixin-B.

Surfaces which can be protected using the method of the invention include ship hulls, pilings, glass and other transparent observation windows, sonar domes, water-conducting pipes, cooling towers and ponds, pumps, valves, filtration members and all other aquatic apparatuses which have surfaces which come into contact with aquatic environments containing fouling organisms. These surfaces may be made of diverse materials such as glass, concrete, steel, wood, fluorocarbons, fiberglass, (especially structured, i.e., resin impregnated, fiberglass) silicone, plastics, fibers (such as hemp fibers), and such materials as generally comprise separatory or filtration membranes, such as polysulfone, nylon, and other polymers. Protection against fouling is generally most desired when the surface being protected is smooth and non-porous (such as a boat hull) since such surfaces, particularly those designed for travel through the water, operate best when their smooth surfaces are maintained so as to reduce drag. However, other surfaces may also be protected according to the teachings of the present invention.

The method of affixing the active ingredients set forth above to the surface being protected is not essential so long as the biological activity of the active ingredient is maintained and the active ingredient is present in sufficient surface concentration to provide protection of the surface against attachment of the fouling organism against which protection is sought.

The methods of this invention as set forth above comprise an approach to control of fouling that has reduced toxic effects in that the materials of this invention are active in a bound state. Prior art teaches that bonding of materials that can be used as antifoulants can be accomplished. Those skilled in the art have considerable experience in attaching anti-foulants to aquatic surfaces to allow for slow release of compounds that, unlike those compounds used in the present invention, are not active when affixed to the aquatic surface. For example, De Graaf, U.S. Pat. No. 4,221,839, discloses a method for anti-fouling which involves coating an appropriate surface with a paint composition which has as its active agent a toxic lead or tin derivative. The slow release of the toxic agent into the local environment is controlled by the balance of water-soluble and water-insoluble binders which are included in the polymer base. Bonding such that slow release does not occur can clearly be accomplished by controlling the balance of the binders. Dawans, U.S. Pat. No. 4,389,460, discloses a method of anti-fouling which involves the use of a polymeric support, such as a polychlorobutadiene and at least one grafted organic chain attached to the polymer. Although the organic chain of this patent contains an organotin group as a toxic agent, it could easily be modified to provide for covalent attachment of one of the biologically active materials of the present invention as listed in Table III. Honda, U.S. Pat. No. 4,383,053, discloses an anti-fouling paint which is based on a fumaric acid ester polymer. The polymeric support is slowly water-soluble so that the coating lasts for a long time. This illustrates that the toxic metallic compound described in the patent (or any other active ingredient) can be maintained within a coating. As in DeGraff, U.S. Pat. No. 4,389,460, the toxic metallic compound has activity only when released, in contrast to the chemicals useful in this invention. These three patents are typical of the state of the art in anti-fouling paints and compositions and exemplify some of the many means already available for affixing an active ingredient to a surface. Accordingly, these patents listed above as well as the following patents which further exemplify methods of attaching active materials to surfaces being protected are herein incorporated by reference: U.S. Pat. No. 4,168,174, U.S. Pat. No. 4,154,818 U.S. Pat. No. 3,979,354, U.S. Pat. No. 3,684,752, and U.S. Pat. No. 3,167,473.

In addition to the patents listed above which discuss the use of various matrices for affixing previously used toxic materials to aquatic surfaces, it is also known in the art to attach various organic chemicals and biochemicals to matrices in arts other than aquatic fouling contexts. For example, many types of chemical reactors which maintain biologically active chemicals in their active forms are known. These include enzyme reactors, ion exchange columns, and the like. For example, U.S. Pat. Nos. 4,237,299, 4,312,946, 4,342,834, and 4,404,296 all disclose the attachment or incorporation of biological materials to or in polyurethane polymer matrices. Further, U.S. Pat. No. 3,843,443 teaches the preparation of polypeptide materials bound to fluorocarbon polymers. In like manner, many of the nonproteinaceous bioactive materials of Table III could be bound to a fluorocarbon support. Although none of these patents disclose the use of the bioactive materials of the present invention, they do demonstrate knowledge by those skilled in the art of enzyme technology for attaching enzymes and other biologically active molecules to other types of surfaces. Accordingly, these patents are likewise incorporated herein by reference for the purpose of illustrating methods of affixing the active ingredients of the present invention to the surfaces being protected. All patents and other publications identified in this application are indicative of the knowledge and level of skill of those who practice in the fields most closely related to this invention and are herein individually incorporated by reference to the same extent as if incorporation by reference were specifically mentioned at the location of each publication.

When the method of the invention is carried out by affixing the biologically active chemical to the surface by means of a matrix which either incorporates the biologically active material by physically entrapping it in the matrix or which is bound to the biologically active material by a chemical bond (whether a polar interaction, ionic bond or covalent bond), a matrix prepared from a polyurethane polymer is a preferred matrix. Especially preferred are hydrophilic polyurethane prepolymers, since these materials can be used to physically entrap biologically active material by mixing the biologically active material with water by which the prepolymer is polymerized. Either foam-, gel-, or film-forming prepolymers may be used. These terms refer to the consistency of the final polymer formed from the prepolymer. Specific examples of hydrophilic prepolymers useful for carrying out this invention and a more specific description of the process of using them are set forth in the examples which follow.

A composition claimed as being novel to this invention is a paint or coating achieved by mixing a hydrophilic polyurethane prepolymer, which can entrap proteins and enzymes in many cases without appreciable loss of functionality, and then, before polymerization is complete, mixing this with a material such as latex or enamel paint, varnish, metal primer or similar paint compounds. As set forth in the examples which follow, a smooth coating or paint can be formulated, with a surfactant in some cases facilitating the mixing and also contributing to the antifouling properties of the coating so achieved.

Also preferred are compositions known to be suitable for use as paints. Several paint compositions are described in the patents listed above and can be used in carrying out this invention when the toxic materials described therein are replaced with the biologically active chemicals of the present invention. Since many of these paints are designed to be slowly eroded by the action of the aquatic environment and to thereby expose the active ingredient physically incorporated therein to the environment at the surface being protected without requiring that the active ingredient be chemically attached to the paint itself, such compositions are preferred for carrying out the invention. The white pigment in many paints, titanium dioxide, and a common thixotropic, colloidal silicon dioxide, are in some cases suitable supports for the bioactive chemicals of interest. Physical entrapment of the active ingredient in a matrix is accordingly a preferred embodiment of the present invention.

Nevertheless, it is also possible to chemically couple the biologically active ingredients to the matrix (or as described below to the surface itself). Chemical methods of attachment will naturally vary depending on the functional groups present in the biologically active ingredient and in the matrix. Many such methods exist. For example, methods of attaching proteins (such as enzymes) to other substances are described in O'Sullivan et al, *Methods in Enz.* 73:147–166 (1981) and Erlanger, *Methods in Enz.* 70:85–104 (1980), which are herein incorporated by reference. While it is possible to design specific couplings to reduce the amount of biological inactivation which takes place to a minimum, even devices such as random coupling using highly reactive species such as carbene or nitrene coupling agents will result in effective surface protection if the biologically active material is added in surplus so that random orientation of the biologically active material will result in a sufficient number of active sites to produce the desired result. When random coupling is used, a three-fold excess, preferably a five-fold excess, of the active ingredient is preferred. Examples of specific attachments which have been shown to be effective in producing anti-fouling surfaces are set forth in the following examples although the present invention is not limited only to these examples.

The invention now being generally described, the same will be better understood by reference to certain specific examples which are included herein for purposes of illustration only and are not intended to be limiting of the invention or any embodiment thereof, unless those specified.

EXAMPLES

Example I
Antifouling Coatings Using Immobilized Enzymes:
 Field Experiments
 The following enzymes were immobilized in polyurethane gels: Chitinase, Subtilisin, Pronase, Trypsin, $\alpha,\beta$-glucosidase, catalase. Water, where used, was distilled. Enzyme activities were not assayed separately.
Polyurethane Coating Preparation:
 no enzyme: 54 ml $H_2O$+7 ml hydrophilic polyurethane prepolymer (non-foaming)
 for pronase: 44 ml $H_2O$+6 ml prepolymer+50 mg pronase (Lot #400899 Calbiochem B grade)
 for trypsin: 44 ml $H_2O$+6 ml prepolymer+50.1 mg trypsin (Lot T-8253 Bovine pancreas σ)
 for subtilisin: 44 ml $H_2O$+6 ml prepolymer+50.0 mg subtilisin (Lot P-5255 σ)
 for chitinase: 44 ml $H_2O$+6 ml prepolymer+50.0 mg chitinase (Lot C-6137 σ)
 for catalase: 44 ml $H_2O$+6 ml prepolymer+50.1 mg catalsae (no lot listed)
 for BSA: 44 ml $H_2O$+6 ml prepolymer+50 mg bovine serum albumin (BSA) (Lot A-6003 type F)

Gels in each case were poured into small petri dishes to form coatings for analysis. These were screwed onto plastic slides and placed in 2 racks in the estuary. Placed in estuary 7 April. Retrieved 19 May, counted immediately thereafter to determine relative settlement.

Arrangement: (Enzymes Used are those Indicated by Abbreviated Reference)

Wheel 1

| | | |
|---|---|---|
| 1 tryp | 10 ceramic | 19 subtil |
| 2 subt | 11 no enzyme | 20 plastic |

-continued

| | | |
|---|---|---|
| 3 cat | 12 plastic | 21 pro |
| 4 chit | 13 ch.it | 22 catal |
| 5 BSA | 14 plastic | 23 subtil |
| 6 tryp | 16 BSA | 24 chit |
| 7 pro | 16 ceramic | 25 pro |
| 8 ceramic | 17 no enzyme | 26 catal |
| 9 tryp | 18 BSA | 27 no enzyme |
| Wheel 2 | | |
| 1 chit | 10 chit | 19 cer |
| 2 no enzyme | 11 catol | 20 plastic |
| 3 pron | 12 no enzyme | 21 plastic |
| 4 pron | 13 catal | 22 no enzyme |
| 5 chit | 14 ceramic | 23 subtil |
| 6 subtil | 15 BSA | 24 tryp |
| 7 ceramic | 16 B#A | 25 plast |
| 8 tryp | 17 tryp | 26 sub |
| 9 BSA | 18 pro | 27 cat |

Numbers of settling organisms per test plate

| | | Balanus | | Schizoporella | | Bugula neritina | | Bugula avicularia | | Styela | | Ascidia | |
|---|---|---|---|---|---|---|---|---|---|---|---|---|---|
| Wheel no. | → | 1 | 2 | 1 | 2 | 1 | 2 | 1 | 2 | 1 | 2 | 1 | 2 |
| Trypsin | 1 | 6 | 11 | 26 | 27 | 21 | 9 | 5 | 0 | 41 | 14 | 2 | 0 |
| in poly- | 2 | 16 | 25 | 40 | 25 | 13 | 11 | 2 | 2 | 35 | 4 | 1 | 0 |
| urethane | 3 | 8 | 25 | 20 | 18 | 10 | 9 | 6 | 1 | 23 | 1 | 0 | 0 |
| | mean | 10 | 20.3 | 29.3 | 23.3 | 14.6 | 9.7 | 4.3 | 1 | 33 | 6.3 | 1 | 0 |
| Subtilysin | 1 | 12 | 13 | 49 | 27 | 16 | 15 | 8 | 0 | 55 | 20 | 0 | 0 |
| in poiy- | 2 | 11 | 10 | 33 | 37 | 8 | 8 | 1 | 4 | 51 | 0 | 3 | 0 |
| urethane | 3 | 8 | 16 | 24 | 27 | 13 | 7 | 3 | 0 | 23 | 35 | 2 | 0 |
| | mean | 10.3 | 13 | 35.3 | 30.3 | 12.3 | 10 | 4 | 1.3 | 4.3 | 18.3 | 1.7 | 0 |
| Catalase | 1 | 7 | 31 | 26 | 38 | 13 | 23 | 3 | 1 | 37 | 2 | 2 | 0 |
| in poly- | 2 | 9 | 29 | 46 | 16 | 12 | 17 | 3 | 8 | 17 | 2 | 0 | 1 |
| urethane | 3 | 9 | 18 | 35 | 24 | 7 | 6 | 1 | 1 | 39 | 12 | 0 | 0 |
| | mean | 8.3 | 26 | 35.7 | 26 | 10.7 | 15.3 | 2.3 | 3.3 | 31 | 5.3 | 0.7 | 0.3 |
| Chitinase | 1 | 0 | 8 | 20 | 19 | 5 | 6 | 3 | 0 | 19 | 12 | 1 | 2 |
| in poly- | 2 | 0 | 4 | 20 | 15 | 5 | 4 | 1 | 1 | 28 | 13 | 0 | 1 |
| urethane | 3 | 0 | 1 | 21 | 32 | 8 | 6 | 0 | 6 | 30 | 11 | 2 | 2 |
| | mean | 0 | 4.3 | 20.3 | 22 | 6 | 5.3 | 1.3 | 2.3 | 25.7 | 12 | 1 | 1.7 |
| Pronase | 1 | 3 | 9 | 42 | 17 | 8 | 9 | 3 | 2 | 29 | 20 | 1 | 1 |
| in poly- | 2 | 3 | 15 | 24 | 28 | 10 | 15 | 3 | 1 | 29 | 18 | 0 | 3 |
| urethane | 3 | 9 | 24 | 26 | 28 | 10 | 11 | 2 | 4 | 50 | 0 | 0 | 0 |
| | mean | 5 | 16 | 30.7 | 24.3 | 9.3 | 11.7 | 2.7 | 2.3 | 36 | 12.7 | 0.3 | 1.3 |
| B.S.A. | 1 | 3 | 34 | 32 | 19 | 12 | 6 | 9 | 0 | 65 | 32 | 6 | 1 |
| in poly- | 2 | 5 | 20 | 25 | 24 | 6 | 12 | 5 | 3 | 23 | 11 | 3 | 0 |
| urethane | 3 | 5 | 13 | 36 | 37 | 5 | 9 | 0.2 | 31 | 4 | 1 | 0 | 0 |
| | mean | 4.3 | 22.3 | 31 | 26.7 | 7.7 | 9 | 4.7 | 1.7 | 39.7 | 15.7 | 3.3 | 0.3 |
| Plain | 1 | 13 | 79 | 26 | 21 | 7 | 6 | 4 | 5 | 30 | 10 | 1 | 0 |
| Poly- | 2 | 11 | 52 | 36 | 15 | 9 | 6 | 4 | 2 | 58 | 11 | 4 | 0 |
| urethane | 3 | 2 | 100 | 34 | 37 | 12 | 7 | 3 | 4 | 37 | 1 | 0 | 0 |
| | mean | 8.6 | 77 | 32 | 24.3 | 9.3 | 6.3 | 3.7 | 3.7 | 41.7 | 7.3 | 1.7 | 0 |
| Ceramic | 1 | 24 | 56 | 35 | 3 | 12 | 4 | 4 | 2 | 16 | 1 | 0 | 0 |
| | 2 | 39 | 49 | 30 | 7 | 9 | 6 | 4 | 1 | 13 | 2 | 2 | 0 |
| | 3 | 41 | 49 | 20 | 15 | 7 | 2 | 5 | 0 | 6 | 0 | 0 | 0 |
| | mean | 34.7 | 51.3 | 28.3 | 8.3 | 9.3 | 4 | 4.3 | 1 | 11.7 | 1 | .7 | 0 |

In conclusion, it can be seen tha the polyurethane support matrix was significantly less attractive to most larval members of the fouling community than ceramic substrates. Certain of the immobilized enzymes, notably chitinase and pronase, were significantly less fouled than the plain polyurethane, and the effect was species specific.

Example II
Anti-fouling Coatings Using Immobilized Enzymes and Tannins: Laboratory Experiments Using Bugula Larvae The experimental substances were subtilisin, chitinase, bovine serum aluminum (BSA) and tannic acid, independently immobilized in polyurethane gels. Enzyme activities were not assayed independently.

Polyurethane Coating Preparation:
no enzyme: 30 ml $H_2O$ dist+4½ml hydrophilic polurethane prepolymer
w/BSA: 17 ml $H_2O$+4½ ml prepolymer+0.035 g BSA
w/subtil: 30 ml $H_2O$+4½ ml prepolymer+0.0350 g Subtil
w/chitimose: 30 ml $H_2O$+4½ ml prepolymer+0.0349 g Chitinase
w/tannin: 30 ml $H_2O$+4½ ml prepolymer+0.35 g tannin Coatings were prepared as in Example I. For comparison, uncoated plexiglas plates were also used, roughened with 100-grade steel wool. The experiment was done on a turntable rotating at ~1.2 rev/min. Seawater flow rate was 325 ml/min. Substrates to be assayed were placed upside down on a rack in the water.

Arrangement:
1 plexiglas
2 plexiglas
3 tannin
4 BSA
5 chit
6 chit
7 plexiglas
8 subtil
9 gel
10 chit
11 BSA
12 gel
13 subtil 14 subtil 15 gel

16 BSA 17 tannin 18 tannin

Bugula Larvae added 16 Oct 10:00 AM–noon

16 Oct 1:30 PM–2:30 p.m.

17 Oct 10:00 AM–2:00 p.m.

18 Oct 9:30 AM–11:00 a.m.

Results:

|  | Replicate No. | | | |
| --- | --- | --- | --- | --- |
| Substrate | 1 | 2 | 3 | Mean |
| Plexiglas | 15 | 12 | 5 | 10.7 |
| Polyurethane without enzyme | 1 | 0 | 0 | 0.3 |
| Subtilisin | 0 | 0 | 0 | 0 |
| Chitinase | 1 | 0 | 0 | 0.3 |
| BSA | 0 | 0 | 1 | 0.3 |
| Tannin | 0 | 1 | 4 | 1.7 |

As can be seen from the tabulated results, over the time period analyzed the polyurethane coatings were much less attractive than the uncoated plexiglas. The low numbers of setting organisms did not allow differentiation between enzymes.

Example III

Background Studies on Larval and Adult Barnacle Attachment on Non-Toxic Anti-fouling Coatings The barnacle was selected as the test organism because it is an important member of the fouling community and because more is known about the chemistry of its substratum cement than is known about that of any other fouling organism. Adult barnacle cement is 70–95% protein; the carbohydrate and lipid elements of the cement are usually negligible ($\leq 2\%$). The mechanism(s) involved in hardening of the cement are not well understood but may consist of protein cross-linking by phenolic groups or by the sulfydryl groups of the constituent amino acids. The larval barnacle substratum adhesive also appears to be predominantly proteinaceous and may also harden by a protein-phenolic group cross-linking mechanism. However, the larval adhesive appears to consist of alkaline proteins rather than acidic proteins as found in the adult cement.

The chemicals used in the experiments designed to test the anti-fouling capability of immobilized chemicals were selected on the basis of their potential ability to interfere with some aspect of the growth, development, or adherence of the barnacle to the substratum. These chemicals and their potential anti-fouling effects are listed in Table V.

TABLE V

Immobilized Chemicals and Their Potential Influence On the Process of Barnacle Adhesion

| Chemical | Potential Action |
| --- | --- |
| Streptomyces protease | degrade adhesive |
| Papaya protease | degrade adhesive |
| Subtilisin | degrade adhesive |
| Chitinase | block information of barnacle's basal immbrane |
| Kojic acid | prevent phenol-protein cross-linking |

TABLE V-continued

Immobilized Chemicals and Their Potential Influence On the Process of Barnacle Adhesion

| Chemical | Potential Action |
| --- | --- |
| Gentisic acid | prevent phenol-protein cross-linking |
| Tresyl chloride | weaken bond between cement and substratum |
| Iodine | toxicant capable of being immobilized |

Methods and Materials

A. Attachment of Adult Barnacles

Adult *Balanus amphitrite* were collected from dock pilings in the vicinity of the Duke University Marine Laboratory and scrubbed clean with a toothbrush. Cleaned barnacles were positioned within 1–2 cm holes drilled in 24×3×0.25 cm Plexiglas strips. The base of each hole was covered with a membrane of masking tape. Each barnacle was pushed through pre-cut slits in the tape membrane until its base was flush with the underside of the Plexiglas strip. The masking tape served to secure the barnacles within the oversized holes in the Plexiglass. The test substrata were placed along the underside of each Plexiglas holder so that the bases of the contained barnacles, rested on the surface of the test substrata. The substrata were held in place with small rubber bands. The contact surface of each substratum was either bare (untreated), or was coated with the immobilized chemical, or coated with just the immobilization matrix. Each holder apparatus was placed within a 28×12×8 cm plastic tank filled with seawater. The barnacles faced downward into the seawater. Food (larvae of the brine shrimp *Artemia salina*) and water were changed daily; the seawater was unfiltered and was kept at room temperature (20–25° C.).

The test substrata (bearing attached barnacles) were disengaged from the Plexiglas holders after 14–21 days. A barnacle was considered to be attached if it could resist the vertical pull of a 113.5 gm lead weight.

B. Attachment of Larval Barnacles

Larvae of *B. amphitrite* were reared en masse from hatching according to the method of Moyse, Nature, Lond. 185:120 (1960). Larvae which had developed to the cyprid state—the stage at which settlement (permanent attachment to a substratum) and metamorphasis occurs—were kept at 4° C. until needed for experimentation. Twenty-five to one-hundred-plus cyprids were added to 5×0.9 cm plastic disposable petri dishes containing 0.45-$\mu$m-Millipore-filtered 33% seawater, and maintained at 25° C. for the duration of the experiment.

The Petri dishes were treated in the same way as the adult barnacle test substrate. In the initial experiments, 50 $\mu$l of a "settlement factor" was added to the water in each dish. This factor stimulates the cyprid larva to (attempt to) attach to the substratum. The settlement factor is a mixture of unidentified water soluble macromolecules derived from a tissue homogenate of adult barnacles. Settlement factors are considered to be important site-recognition signals and settlement-inducers for many species of marine invertebrate larvae.

An experiment lasted 24 to 96 hours. Since the actual settlement event occurs rapidly and is an all-or-nothing event, larval attachment was evaluated by counting the number of settled larvae at the end of the time priod.

C. Preparation of the Immobilized Chemicals in Polyurethane

The immobilization matrix was made by combining a hydrophilic polyurethane prepolymer (HYPOL$^R$; WR Grace and Co.) with either deionized water or acetone. Chemicals were immobilized by adding them to the water or acetone prior to mixing with the prepolymer. The final concentration of all immobilized chemicals was 5 mg/ml, unless otherwise indicated.

Two classes of polyurethane prepolymers were used: foam-forming prepolymers and gel-forming prepolymers. These terms refer to the consistency of the final polymer when the prepolymer is mixed with water or acetone. The prepolymers used, and the proportions of the prepolymer and the water or acetone, are listed in Table VI. The prepolymer and the desired bioactive chemical were mixed in disposable plastic beakers and either painted on the substratum or poured into disposable plastic Petri dishes. Initial polymerization is evident within a few minutes after mixing; polymerization is complete 24–72 hours later, depending upon the amount of water or acetone used. These coatings are qualitatively identical to those used in Examples I and II.

TABLE VI

Prepolymer Types and Formulations Used for The Immobilization Matrices

| Prepolymer Type | Mixing Agent | Ratio of Ingredients Prepolymer vol: Solvent vol. |
| --- | --- | --- |
| Gel X81680 | water or acetone | 1:29 |
| Foam 2000 | water or acetone | 1:1 |
| Foam 2002 | water or acetone | 1:1 |
| Foam 4100 | water or acetone | 1:1 |
| Foam 4200 | water or acetone | 1:1 |
| Foam 5000 | water or acetone | 1:1 |

D. Covalent Linkage of Papaya Protease to a Wood Substratum

Strips of fir wood were painted twice with "dry acetone" prepared by mixing reagent grade acetone with molecular sieves type 4 Å Grade 516. The wood surface was then activated by painting onto it a mixture of tresyl chloride (1 ml), pyridine (2 ml), and dry acetone (500 ml), followed by a series of acid acetone washes and sealed in a desiccated container until use. "Control" wood strips were dipped in deionized water, while "test" strips were painted with solutions of chitinase, bacterial protease or papaya protease and allowed to react for 10 minutes before water rinsing. These strips were used in adult barnacle attachment assays.

E. Measurement of the Enzymatic Activity of Immobilized Bacterial and Papaya Proteases The in vitro activities of bacterial and papaya proteases were assayed before and after immobilization by monitoring pH changes associated after substrate addition. The exact protocol for these assays of enzyme activity is that described by the supplier of the enzyme, Sigma Chem. Co., St. Louis, Mo.

Results:

A. Effect of the Polyurethane Prepolymer Type on Barnacle Substratum Attachment.

1. Adult *Balanus amphitrite*

An essential feature of the immobilization matrix is that it is chemically inert and hence does not interfere with attachment process. The experiments discussed here compare the atttachment responses of adult and larval barnacles to different types of polyurethane matrices. Data on the attachment of adult *Balanaus amphitrite* to the treated and untreated substrata are presented according to type of substratum (eg. glass, Plexiglas). This division of the data is a reflection of the chronological order of the anti-fouling research, in which all initial research on adults exclusively involved glass as a test substratum, while more recently has included alternative substrates (principally polyvinyl chloride and Plexiglas).

Table VII summarizes the data on the effect of prepolyiner type on adult barnacle attachment to glass. The mean (X) and standard deviation (S) were computed using the arcsine transforms of the original attachment percentage values.

TABVLE VII

The Effect of Prepolymer* Type on Adult *Balanus amphitrite* Substratum Attachment

| | | % Attached | | | |
| --- | --- | --- | --- | --- | --- |
| Treatment | Substratum | X$^1$ | S | N | R |
| (Batch) Hydro Gel X8168D (with acetone) | glass | 30.1 | 11.3 | 23 | 3 |
| (Batch) Hydro Gel X8168D (with water) | glass | 40.7 | 18.6 | 24 | 3 |
| Hypol Foam 2002 (with acetone) | glass | 0.0 | 0.0 | 24 | 3 |
| Hypol Foam 2002 (with water) | glass | 42.4 | 6.0 | 24 | 3 |
| Untreated | glass | 33.1 | 18.8 | 24 | 3 |

*Prepolymers as manufactured by Grace Chemical Co.

Attachment of adults to glass coated with either the water-based gel or the water-based foam matrix without immobilized enzymes was not signicantly different from that of the untreated control glass surface (Table VIII). However, large differences in adult attachment occurred among the acetone-based matrices, in which no attachment was observed on glass coated with the Hypol foam 2002 matrix formulated with acetone.

TABLE VIII

The Effect of Prepolymer Type and water vs acetone formulations on Adult *Balanus amphitrite* Substratum Attachment. An Analysis of Variance was Done to Test for Significant Differences In Attachment to the Various Matrices (Date shown in Table VII)

| Source of Variation | df | ss | MS | F |
| --- | --- | --- | --- | --- |
| Among water based matrices | 2 | 147 | 73.6 | 0.46 ns$^1$ |
| Within water based matrices | 6 | 951 | 158.5 | |
| TOTAL | 8 | | | |

| Source of Variation | df | ss | MS | F |
| --- | --- | --- | --- | --- |
| Among acetone based matrices | 2 | 2010.6 | 1005.3 | 6.27* |
| Within acetone based matrices | 6 | 961.6 | 160.3 | |
| TOTAL | 8 | | | |

*$P < 0.05$
$^1$Abbreviations used are ns = not significant, P = probability the results are due to chance.

Attachment of adult *B. amphitrite* to coated wood (oak), gray PVC (polyvinyl chloride), Plexiglas, and glass is compared in Table IX. The foam prepolymers used were considered less reactive than the foam 2002 prepolymer used earlier (Table VII). Antifoaming agents were incorporated into some of the matrices in an attempt to minimize the generation of the surface irregularities which are characteristic of the foam matrix. Attachment of adults to the uncoated substrata was surprisingly low. Consequently, a rigorous statistical analysis of the data is not warranted, and only obvious trends in the data will be discussed.

TABLE IX

Effect of prepolymer type and substratum on adult *Balanus amiphitrite* attachment.

| Treatment | Substratum | % Attached | | | | % Dead | | | |
|---|---|---|---|---|---|---|---|---|---|
| | | $X^1$ | S | N | R | X | S | N | R |
| Foam 4100 | glass | 26.8 | 5.9 | 24 | 3 | 16.4 | 4.4 | 24 | 3 |
| Untreated | glass | 25.9 | 3.4 | 24 | 6 | 25.3 | 4.2 | 24 | 6 |
| Foam 4100 | Plexiglas | 0.0 | 0.0 | 24 | 3 | 3.9 | 6.8 | 24 | 3 |
| Foam 4100 + Antifoam A[2] | Plexiglas | 9.5 | 8.5 | 24 | 3 | 16.7 | 0.0 | 24 | 3 |
| Foam 4100 + Antifoam H 10[2] | Plexiglas | 8.0 | 13.8 | 24 | 3 | 23.8 | 5.4 | 24 | 3 |
| Foam 5000 | Plexiglas | 5.6 | 9.6 | 24 | 3 | 5.6 | 9.6 | 24 | 3 |
| Foam 5000 + Antifoam A | Plexiglas | 7.8 | 6.8 | 24 | 3 | 40.1 | 6.5 | 24 | 3 |
| Foam 5000 + Antifoam H 10 | Plexiglas | 22.5 | 5.3 | 24 | 3 | 30.6 | 13.0 | 24 | 3 |
| Untreated | Plexiglas | 11.8 | 9.3 | 24 | 6 | 15.4 | 9.6 | 24 | 6 |
| Foam 4100 | PVC | 16.4 | 4.5 | 24 | 3 | 18.0 | 2.3 | 24 | 3 |
| Foam 4100 + Antifoam A | PVC | 21.8 | 1.9 | 24 | 3 | 18.0 | 2.3 | 24 | 3 |
| Foam 4100 + Antifoam H 10 | PVC | 19.8 | 7.7 | 24 | 3 | 13.4 | 2.8 | 24 | 3 |
| Foam 5000 | PVC | 0.0 | 0.0 | 24 | 3 | 9.5 | 8.6 | 24 | 3 |
| Foam 5000 + Antifoam A | PVC | 0.0 | 0.0 | 24 | 3 | 17.0 | 14.8 | 24 | 3 |
| Foam 5000 + Antifoam H 10 | PVC | 9.5 | 8.6 | 24 | 3 | 13.4 | 2.8 | 24 | 3 |
| Untreated | PVC | 24.2 | 4.9 | 24 | 9 | 21.7 | 13.2 | 24 | 9 |
| Foam 4100 | Oak Wood | 16.4 | 4.5 | 24 | 3 | 15.1 | 2.8 | 24 | 3 |
| Untreated | Oak Wood | 29.7 | 5.6 | 24 | 3 | 12.5 | 10.9 | 24 | 3 |

[1]Abbreviations used are; X = mean; S = standard deviation; N = number of animals per experiment; R = number of replicate experiments. The mean and standard deviation were computed using the arcsine transforms of the original data.
[2]1 ml antifoaming agent was added to 10 mls of prepolymer and mixing agent.

Attachment percentage values were similar among the uncoated glass, wood and PVC substrata. However, attachment to uncoated Plexiglas was 2–3 times lower than all other substrata tested. The presence of a polyurethane matrix resulted in lower attachment success for all substrata except glass. The addition of an antifoaming agent (particularly antfoaming agent H-109), however, generally acted to slightly increase attachment success.

III. A. Effects of the Polyurethane Prepolymer Type on Barnacle Substratum Attachment (Continued)

2. Larval *Balanus amphitrite*

These experiments on larval settlement involved the use of an "attractant," which was added to both experimental and control substrata. The attractant is prepared from the tissues of the adult barnacle and functions to stimulate settlement and metamorphosis in cyprid larva. The results of these experiments are given in Table X.

TABLE X

The effect of prepolymer* type without immobilized enzymes on settlement of *B. amphitrite* cyprids

| Treatment | Substratum | Attachment | | | |
|---|---|---|---|---|---|
| | | $X^1$ | S | N | R |
| Hydro-Gel X8168D (with water) | plastic Petri dish | 10.4 | 8.3 | 24–112 | 5 |
| Hydro-Gel X8168D (with acetone) | plastic Petri dish | 13.4 | 23.2 | 25–44 | 3 |
| Hypol Foam 2000 (with acetone) | plastic Petri dish | 33.5 | 11.8 | 93–112 | 3 |
| Hypol Foam 2002 (with acetone) | plastic Petri dish | 37.5 | 5.10 | 22–104 | 4 |
| Hypol Foam 4100 (with acetone) | plastic Petri dish | 40.7 | 11.0 | 25–126 | 4 |
| Hypol Foam 4200 (with acetone) | plastic Petri dish | 38.0 | 9.0 | 27–114 | 4 |
| No coating | plastic Petri dish | 50.3 | 11.8 | 37–143 | 5 |

[1]Abbreviations used are: X = means; S = standard deviation; N = number of animals per experiment; R = number of replicate experiments. The mean and standard deviations were computed using the arcsine transforms of the orginal percentage values.
*Prepolymers as manufactured by Grace Chemical Co. In these experiments all substrata tested were treated with an "attractant" (see text for details).

Large differences in cyprid settlement percentage were found among the prepolymer treatments (Table XI). These differences were a consequence of the small numbers of cyprids which settled on the Hydro-gel prepolymer which had been mixed with either water or acetone. Rinsing the dishes containing the gel polymer with methanol, or soaking the dishes in deionized water for 24 hours did not effect an improvement in larval settlement. Settlement on the foam polymers without immobilized enzymes was not significantly different from controls (Table XII).

TABLE XI

The Effect of Prepolymer Type on Settlement of
B. amphitrite. An Analysis of Variance was done in
Order to Determine if the Average Settlement
Percentage Differed Significantly Among the Types
of Prepolymers Used

| Source of Variation | df | ss | MF | F |
|---|---|---|---|---|
| Among prepolymer groups | 6 | 4963.32 | 827.22 | 6.06 |
| Within prepolymer groups | 21 | 2865.53 | 136.45 | |
| TOTAL | 27 | 7828.85 | | |

$P < 0.001$
df = degress of freedom
ss = sum of squares
MS = mean-square
F = F-statistic, =
MS (among group)
MS (within groups)
P = probability estimated from F-table values

TABLE XII

The effect of prepolymer type
on settlement of B. amphitrite

| Gel (water) | Gel (acetone) | Foam 2000 | Foam 2002 | Foam 4200 | Foam 4100 | Control |
|---|---|---|---|---|---|---|
| 3.26* | 5.40 | 30.50 | 37.1 | 37.7 | 42.5 | 58.6 |

*A Student-Newman Kuels test was done in order to test for statistically significant differences between specific mean settlement percentages. The mean values, and their corresponding prepolymer type, are listed below in order of increasing percentage value. Those means which are underlined are not significantly different from one another; those means which are not underlined are significantly different from those which are underlined ($P < 0.05$).

The effects of polyurethane matrix type on adult and larval barnacle substratum attachment can be summarized as follows. Attachment percentages were lower on matrices made with acetone than on matrices made with water. Comparable attachment success of adult barnacles occurred on plain grass, and glass coated with the Hydro gel X8168D matrix; in all other cases, attachment was mildly to strongly depressed on substrata coated with a polyurethane matrix, even in the absence of immobilized enzymes. Additionally, larval settlement values were consistently lower on surfaces treated with Hydro gel X8168D matrix than on the controls, while settlement on all other matrices was equivalent to control values.

Results (Continued)

B. Effect of Immobilized Chemicals on Barnacle Substratum Attachment

1. Adult *Balanus amphitrite*

Experiments of the effect of prepolymer type on barnacle substratum attachment produced opposing results among adult and larval barnacles. Adults attached in the absence of immobilized enzymes in greatest numbers to the Hydro gel X8168D matrix, while larval attachment was lowest on this matrix, and highest on the Hypol-based foam 4100 matrix. In order to compensate for these differences in matrix influences on substratum attachment, both the gel X8168D and the foam 4100 were used in the experiments to determine the effect of immobilized chemicals on adult barnacle attachment.

The effect of chemicals immobilized in the gel X8168D matrix on substratum attachment of adult barnacles is listed in Table XIII. Differences in substratum attachment of adult *B. amphitrite* across treatments are highly significant (Table XIV). The average percentage of attachment of barnacles exposed to glass surfaces coated with immobilized Streptomyces protease, chitinase, or iodine were 2–5 times less than that of the polyurethane and plain glass controls. In the absence of immobilized chemicals, approximately equal numbers of barnacles attached to the polyurethane-treated and the untreated glass slides.

TABLE XII

Effect of immobilized chemicals
on adult B. amiphitrite
substratum attachment

| | | % Attached | | | | % Dead | | | |
|---|---|---|---|---|---|---|---|---|---|
| Treatment | Substratum | $X^1$ | S | N | R | X | S | N | R |
| Gentisic Acid | glass | 49.9 | 0.7 | 24 | 3 | 15.6 | 7.3 | 24 | 3 |
| Kojic Acid | glass | 39.0 | 10.6 | 24 | 3 | 11.2 | 9.7 | 24 | 3 |
| Tresyl Chloride | glass | 46.4 | 11.1 | 24 | 3 | 12.2 | 7.5 | 24 | 3 |
| Subtilisn | glass | 38.8 | 8.1 | 24 | 3 | 14.9 | 4.2 | 24 | 3 |
| Papaya Protease | glass | 44.1 | 9.9 | 24 | 3 | 16.4 | 4.4 | 24 | 3 |
| Streptanyces Protease | glass | 12.5 | 13.9 | 24 | 6 | 24.8 | 19.1 | 24 | 6 |
| Chitinase | glass | 19.6 | 20.6 | 24 | 6 | 24.8 | 22.4 | 24 | 6 |
| Iodine | glass | 21.7 | 9.4 | 24 | 6 | 35.3 | 20.2 | 24 | 6 |
| Iodine (15 mg/ml) | glass | 0.0 | 0.0 | 24 | 3 | 41.8 | 2.8 | 24 | 6 |
| Gel X8168D | glass | 41.6 | 12.4 | 24 | 6 | 27.4 | 8.1 | 24 | 6 |
| Untreated | glass | 41.0 | 18.4 | 24 | 9 | 15.8 | 12.3 | 24 | 9 |

[1]Abbreviations used are: X = mean; S = Standard Deviation; N = number of animals per experiment; R = number of replicate experiments. The means and standard deviation were computed using the arcsine transforms of the original percentages values.

The effect of immobilized chemicals on adult *B. amphitrite* substratum attachment is shown in Table XIV. An analysis of variance was done in order to determine if the average attachment percentages differed significantly among the immobilized chemicals used.

TABLE XIV

| Source of Variation | df | ss | MS | F |
|---|---|---|---|---|
| Among chemical groups | 13 | 13570.3 | 1057.72 | 5.9634 |
| Within chemical groups | 46 | 8158.92 | 177.368 | |
| TOTAL | 59 | 21909.3 | | |
| | | | | $P < 0.001$ | df = degrees of freedom
ss = sum of squares
MS = mean-square
F = F-statistic = $\frac{MS \text{ (among group)}}{MS \text{(within groups)}}$
P = probability estimated from F-table values In order to determine if the observed effects of substratum treatment of barnacle attachment were a consequence of differences in the health of the experimental animals, the survivors of the first three replicates of the chitinase, Streptomyces protease, and iodine test groups and the plain-glass control groups were removed from their respective substrata and placed on untreated glass slides. All animals were evaluated for reattachment to the glass surface after 14 days. The results of these experiments are given in Table XV. The average percentage values of attachment and reattachment in the controls were nearly identical; however, the reattachment values for each of the other treatment groups were greater (in some cases 2-3 times greater) than the original attachment values. These results indicate that the observed inhibition of adult barnacle substratum attachment was a consequence of the activity of the immobilized chemicals and not due to the health of the animals.

TABLE XV

Reattachment of adult *B. amphitrite* to plain glass following removal from the treatment substratum

| | | % Attachment | | | |
|---|---|---|---|---|---|
| Original Treatment | Substratum | $X^1$ | S | N | R |
| Chitinase ± | glass | 27.7 | 6.7 | 16–19 | 3 |
| Streptomyces Protease | glass | 36.5 | 6.4 | 19–23 | 3 |
| Iodine | glass | 41.1 | 9.9 | 15–19 | 3 |
| Untreated | glass | 44.9 | 14.9 | 14–22 | 3 |

[1]Abbreviations used are: X = means; S = standard deviation; N = number of animals per experiment; R = number of replicate experiments. The mean and standard deviations were computed from the arcsine transforms of the original percentage values.

The effect of chemicals immobilized in the 4100 foam matrix on adult substratum attachment differed importantly from the effects of chemicals immobilized in the gel X8168D (Table XVI). First, in addition to Streptomyces protease and iodine, the papaya protease and gentisic acid treatments yielded the lowest attachment values of the experimental series. Second, attachment to the matrix and untreated controls was exceptionally low. In view of the latter result, the significance of the data of this series of experiments is unclear. Possible causes of the decline in the adult control attachment values during the course of the anti-fouling research period are discussed in Section IV below.

TABLE XVI

Effect of immobilized chemicals on adult *Balanus amiphitrite* attachment

| | | % Attached | | | | % Dead | | | |
|---|---|---|---|---|---|---|---|---|---|
| Treatment | Substratum | $X^1$ | S | N | R | X | S | N | R |
| Hypol 4100 + Chitinase | PVC | 13.4 | 2.8 | 24 | 3 | 0.0 | 0.0 | 24 | 3 |
| Hypol 4100 + Streptomyces Protease | PVC | 3.9 | 6.7 | 24 | 3 | 18.5 | 7.8 | 24 | 3 |
| Hypol 4100 + Kojic Acid | PVC | 17.3 | 17.6 | 24 | 3 | 7.9 | 6.8 | 24 | 3 |
| Hypol 4100 + Iodine | PVC | 15.0 | 2.8 | 24 | 3 | 3.9 | 6.8 | 24 | 3 |
| Hypol 4100 + Iodine (15 mg/ml) | PVC | 3.9 | 6.8 | 24 | 3 | 12.5 | 11.0 | 24 | 3 |
| Hypol 4100 + Papaya Protease | PVC | 3.9 | 6.8 | 24 | 3 | 0.0 | 0.0 | 24 | 3 |
| Hypol 4100 + Gentisic Acid | PVC | 3.9 | 6.8 | 24 | 3 | 7.9 | 6.8 | 24 | 3 |
| Hypol 4100 | PVC | 6.9 | 12.0 | 24 | 3 | 3.9 | 6.8 | 24 | 3 |
| Untreated[2] | PVC | 26.3 | 9.3 | 24 | 3 | 17.5 | 6.1 | 24 | 3 |

[1]Abbreviations used are X = Mean; S = Standard Deviation; N = Number of animals per experiment; R = Number of Replicate Experiments. The mean and standard deviation were computed from the arcsine transforms of the original percentage values.
[2]The untreated PVC control presented here is that for previous series of experiments.

2. Larval *Balanus amphitrite*

Cyprid settlement varied with the duration of the experiment, the matrix type, and the immobilized chemical. Settlement of cyprids exposed for 24 hours to chemicals entrapped within an acetone-based polyurethane matrix (Foam 4100) was strongly depressed in the chitinase, papaya protease, and iodine treatments, and in the matrix control, relative to that in the untreated controls (Table XVII). However, after 96 hours of exposure, settlement values remained significantly depressed in only the iodine (15 mg/ml) treatment (Table XVIII). In a similar set of experiments involving acetone-based Hypol-based foam 4100 matrices, cyprid settlement was significantly lower in both the Streptomyces protease and the iodine (15 mg/ml) treatments (Table XIX). The average age of the cyprids used in both of these series of experiments was approximately one week.

TABLE XVII

The effect of immobilized chemicals on settlement of *B. amphitrite* cyprids. Acetone based matrices.

| Treatment | Substratum | Duration of Experiment (hours) | % Settlement $X^1$ | S | N | R |
|---|---|---|---|---|---|---|
| Chitinase | plastic petri dish | 24 | 34.2 | 18.2 | 200 | 6 |
|  |  | 96 | 72.2 | 2.3 | 172 | 6 |
| Papaya Protease |  | 24 | 14.9 | 15.2 | 168 | 6 |
|  |  | 96 | 61.3 | 11.9 | 228 | 6 |
| Iodine (low level) |  | 24 | 24.9 | 7.2 | 205 | 6 |
|  |  | 96 | 57.4 | 9.3 | 188 | 6 |
| Iodine (high level) |  | 24 | 24.9 | 7.2 | 157 | 6 |
|  |  | 96 | 6.9 | 7.9 | 166 | 6 |
| Foam 4100 + Attractant[2] |  | 24 | 71.0 | 10.3 | 179 | 6 |
|  |  | 96 | 82.4 | 6.1 | 200 | 6 |
| Foam 4100 |  | 24 | 38.5 | 7.3 | 175 | 6 |
|  |  | 96 | 61.2 | 10.7 | 181 | 6 |
| Untreated |  | 24 | 57.5 | 5.0 | 186 | 6 |
|  |  | 96 | 56.0 | 8.5 | 166 | 6 |

[1]Abbreviations used are: X = mean; S = Standard Deviation; N = number of animals in the experiments; R = number of experiments. The means and standard deviation were computed using the arcsine transforms of the original percentage values.
[2]"Attractant" was added only where indicated.

The effect of immobilized chemicals on settlement of *B. amphitrite* cyprids was also tested using acetone-based matrices. A Student-Newman-Kuels test was done in order to test for statistically significant differences between specific average settlement percentages. The average values, and the corresponding immobilized chemical, are listed below in order of increasing percentage value. Those means which are underlined are not significantly different from one another.

TABLE XVIII

| Iodine (high) | Untreated | Iodine (low) | Foam 4100 | Papaya (Protease) | Chitinase | Foam 4100 + Attractant |
|---|---|---|---|---|---|---|
| 6.95 | 55.9 | 57.4 | 61.2 | 61.3 | 72.2 | 82.4 |

TABLE XIX

The effect of immobilized chemicals on settlement of *B. amphitrite* cyprids. (Acetone-based matrices.)

| Treatment | Substratum | Duration of Experiment (hours) | % Settlement $X^1$ | S | N | R |
|---|---|---|---|---|---|---|
| Chitinase | PLASTIC PETRI DISH | 120 | 39.8 | 6.3 | 19–58 | 6 |
| Iodine (low) | PLASTIC PETRI DISH | 120 | 39.2 | 7.2 | 23–52 | 6 |
| Iodine (high) | PLASTIC PETRI DISH | 120 | 9.9 | 9.5 | 23–35 | 6 |
| Streptomyces Protease | PLASTIC PETRI DISH | 120 | 8.5 | 13.2 | 21–30 | 5 |
| Hypol Foam 4100 + Attractant | PLASTIC PETRI DISH | 120 | 36.0 | 15.2 | 26–40 | 6 |
| Hypol Foam 4100 | PLASTIC PETRI DISH | 120 | 35.0 | 6.3 | 27–67 | 6 |
| Untreated | PLASTIC PETRI DISH | 120 | 45.4 | 10.4 | 24–34 | 6 |

[1]Abbreviations used are X = mean; S = standard deviation; N = number of animals per experiment; R = number of replicate experiments. The mean and the standard deviation were computed from the arcsine transforms of the original percentage values.

Cyprids exposed to chemicals immobiLized in water-based Hypol foam 4100 matrices showed low settlement values in the iodine (15 mg/ml) treatments only (Table XX). Settlement values increased slightly during the course of the experiment in all treatments and controls. The cyprids used in this set of experiments were approximately four weeks old.

TABLE XX

The effect of immobilized chemicals on settlement in *Balanus amphitrite*. Water-based matrices.

| Treatment | Substratum | Duration of Experiment (hours) | % Settlement $X^1$ | S | N | R |
|---|---|---|---|---|---|---|
| Streptomyces Protease | plastic Petri dish |  | 2462.1 | 4.2 | 185 | 3 |
|  |  | 96 | 67.8 | 3.2 | 185 | 3 |
| Papaya Protease | plastic Petri dish |  | 2464.1 | 2.6 | 187 | 3 |
|  |  | 96 | 68.3 | 4.8 | 187 | 3 |
| Iodine (high) | plastic Petri dish |  | 248.98 | 10.1 | 127 | 3 |
|  |  | 96 | 11.7 | 14.7 | 127 | 3 |
| Iodine (low) | plastic Petri dish |  | 2452.8 | 10.8 | 123 | 3 |
|  |  | 96 | 61.9 | 9.5 | 123 | 3 |
| Kojic Acid | plastic Petri dish |  | 2460.3 | 1.9 | 165 | 3 |
|  |  | 96 | 70.0 | 3.9 | 165 | 3 |
| Gentisic Acid | plastic Petri dish |  | 2462.9 | 9.1 | 201 | 3 |
|  |  | 96 | 68.2 | 6.2 | 201 | 3 |
| Foam | plastic Petri dish |  | 2456.9 | 10.2 | 217 | 3 |
|  |  | 96 | 69.3 | 6.6 | 217 | 3 |
| Untreated | plastic Petri dish |  | 2459.7 | 2.7 | 217 | 3 |
|  |  | 96 | 67.5 | 2.4 | 217 | 3 |

[1]The mean and standard deviation are based on the arcsine transformations of the original percentage values.

The increase in settlement values with time of exposure to the treatments within the same set of experiments could be the result of (1) intrinsic variations among cyprids in the time required to initiate and complete the process of settlement, (2) acclimation of the cyprids to the experimental environment, or (3) a change in the experimental environment. If intrinsic developmental variability among the cyprids were the only cause, then the increase in settlement in the treatments should be qualitatively and quantitatively similar to that within the controls. This expectation is observed in the set of experiments which involved settlement on water-based matrices (Table XX), in which control settlement values increased by the same amount as the treatment values. However, in the experiments using acetone-based matrices, settlement in the untreated controls (plain petri dish) did not increase over time, while settlement in the matrix control increased by the same large amount as did most of the treatments. Thus there appears to be a large matrix effect on settlement with acetone-based matrices, and either the cyprids adjust to this factor(s) with time, or the factor(s) is dissipated with time. At present there is not enough information to distinguish between these alternatives.

The large difference in the magnitude of the increase in settlement values with time between the acetone-based matrices and the water-based matrices could be the result of (1) variations in the effect of the different matrix types on cyprid settlement, or (2) differences in the age of the cyprids used in these two set of experiments. It is well known that cyprids settle more readily as they age. However, in spite of the age differences among the cyprids, the settlement percentage values of the untreated (plain dish) controls were similar in both sets of experiments. Thus the nature of the immobilization matrix appears to be the more important determinant of the quantitative differences in the increase in settlement values with time among these experiments.

Results (Continued)

C. Enzymatic Activity of Proteases Immobilized in Polyurethane

As detailed in Example II, an in vitro assay for the enzymatic activity of bacterial protease and papaya protease was conducted. The results, briefly, indicated that (1) these enzymes do maintain their activity upon immobilization, (2) the activity is dependent upon the mode of immobilization, with much-enhanced activity exhibited when the active site was substrate-protected during the immobilization, and (3) that the papaya protease in an immobilized state requires activation by cysteine addition, whereas the bacterial protease does not. The latter finding provides a probable explanation for why the bacterial protease showed more marked anti-fouling effectiveness.

A series of experiments was carried out to test in vitro activity vs concentration of immobilized bacterial and papaya proteases. For both papaya protease and bacterial protease the enzymatic activity increased with increased enzyme concentration. However, the activity per mg of immobilized enzyme decreased with increasing concentration. This is indicative of some of the protein being less reactive at the higher concentration. The most probable explanation is less effective active-site protection during immobilization. A more effective protection could be afforded by use of a reversible competitive inhibitor.

Results (Continued)

D. Effect of a Covalently-bound Protease on Adult *Balanus amphitrite* Substratum Attachment An alternative to immobilization of biologically active chemicals by entrapment within a polyurethane support matrix is by covalently linking the chemicals to the substratum. Preliminary data on the effect of covalently-bound papaya on adult barnacle attachment is presented in Table XXI. There was little difference in attachment percentage between the substratum bearing the covalently bound protease ("activated" wood) and the control ("unactivated" wood) substratum. However, calculations suggest that the surface was in all likelihood very sparsely "coated" with the active enzyme, thereby providing little effective action. Other, more complete, experiments involving covalently bound bioactive materials are presented in Example IV.

TABLE XXI

Attachment of adult *Balanus amphitrite* to fir wood with Papaya Protease covalently attached.

| Treatment | Substratum | % Attached | | | | % Dead | | | |
|---|---|---|---|---|---|---|---|---|---|
| | | $X^1$ | S | N | R | X | S | N | R |
| Activated + Papaya Protease | fir wood | 14.7 | 5.1 | 24 | 3 | 14.7 | 5.1 | 24 | 3 |
| Unactivated | fir wood | 16.4 | 4.3 | 24 | 3 | 15.8 | 7.0 | 24 | 3 |

[1]Abbreviations used are: X = mean; S = standard deviation; N = number of animals per experiment; R = number of replicate experiments. The mean and standard deviation were computed from the arcsine transforms of the original percentage values.

Discussion

The experiments reported as Example III on the effect of enzymes and inorganic toxins immobilized within a polyurethane matrix on adult and larval substratum attachment demonstrates that immobilized, biologically active chemicals have anti-fouling capability. The evidence for this conclusion is as follows:

(1) It was demonstrated that comparable attachment success can occur on untreated control substrata and on substrata coated with a specific type of polyurethane matrix in the absence of immobilized chemicals.

(2) The incorporation of certain chemicals into these same matrices resulted in significantly depressed substratum attachment values. These chemicals were iodine and the enzymes chitinase and Streptomyces protease for adult *Balanus amphitrite* (Table XIII), and iodine and Streptomyces protease for larval *B. amphitrite* (Tables XVII, XIX, XX).

(3) It was demonstrated that an enzyme (*Streptomyces protease*) retains its enzymatic activity as well as anti-fouling action when entrapped within the polyurethane matrix.

(4) The adult barnacle attachment assays, in spite of their variability, served a useful purpose in providing proof-of-principle data on the potential of immobilized bioactive chemicals to impair the cementation process.

Example IV

Studies of Effectiveness of an Immobilized Antibiotic, an Immobilized Ouaternary Ammonium Compound and an Immobilized Protease in Preventing Bacterial Growth and/or Settlement by Marine Invertebrate Larvae Methods Assays for Inhibition of Bacterial Growth The influence of immobilized bioactive species on bacterial growth was first studied by turbidometric assays of the growth of bacterial cultures (*E. coli* or *Staphyloccocus epidermitus*). Inoculation of flasks containing culture media (0.8 g nutrient broth powder to 100 ml water) result in growth curves that can be followed by monitoring the change in turbidity of the shaken suspensions maintained at 37° C. (Culture vessels with side arms were used so that turbidity measurements could be made at intervals without risk of contamination or other interference with the growing bacteria. In these tests, the exposure of the growing cells to silicone, Bion®, controlled pore glass or agarose bead surfaces with an antibiotic, polymixin-B, immobilized on these surfaces resulted in an inhibition of growth as evidenced by a lag period in the growth curve. it should be noted that the innoculum was purposely selected to result in a complete growth curve in any case, i.e., the tests were not designed to allow for cessation of growth but rather for a retardation of growth. Careful rinsing of the treated surfaces and comparison with appropriate controls assured that the lag in growth curves was not due to release of bioactive material from the treated surfaces.

A complementary assay was developed for study of inhibition of bacterial growth on treated surfaces, based upon a measured decrease in the number of colony forming units (CFU) on treated versus untreated surfaces. Surfaces to which bioactive agents have been attached include Silicone, Bion, glass, and poly-styrene. Suspensions of the test bacteria, *Staphylococcus epidermidus*, were placed in 1–10 microliter droplets on test and control surfaces. Droplets were taken to dryness at 37° C. in 1.5 h. The surface was then inverted and applied to a sterile agar plate. The surface/agar plate sandwich was incubated overnight to generate visible colonies. Colonies were counted directly with a dissecting microscope. In addition to assays with untreated (control) surfaces, bacterial suspensions were incubated directly on agar to determine the maximum number of CFU that can be expected. In some laboratory experimentation, sterilization of the surface prior to the assay was carried out to insure that the CFU observed were due to the experimentally added bacteria. Settlement assays for Invertebrate Larvae Bryozoans, *Bugula neritina*

Adult colonies collected from the local environment were incubated at 25° C. overnight in the dark. Larval release from the colonies was induced by light shock. Larvae were placed in 5 ml 100,000 Dalton filtered sea water in treated and untreated polystyrene (Falcon 1006) dishes. Dishes were incubated at 21° C. for 30 minutes and settlement scored. Larvae that have attached and deciliated are counted as settling; those that have not attached and that have not deciliated are counted as not settling.

Barnacles, *Balanus amphitrite*

Barnacle settlement assays were performed as described in Rittschof, et al., *J. Exp. Mar. Biol. Ecol.* 82:131–146 (1984). Briefly, larvae were reared in mass culture in the laboratory on a diet of diatoms (*Skeletonema costatum*). The settling stage, cyprids, are held for 3 days at 4° C. Three-day-old cyprid settlement is approximately 50% on polystrene in a 22 h settlement assay. Larvae irreversibly attached to the substrate are counted as settling, those not permanently attached are counted as not settling.

Immobilization Procedures (a) Dow Corning Quaternary Ammonium Chloride

Quaternary ammonium chloride was applied to surfaces as per the instructions of the manufacturer.

(b) Achromopeptidase

The enzyme achroinopeptidase (supplied by Wako Chemical Co.) was immobilized on glass and plastic substrates by carbodiimide coupling to amino propyl silanized surfaces resulting in covalent attachment. To accomplish this, glass (culture tube and cover glass slips) and plastic (petri dishes) surfaces were acid cleaned in warm dilute nitric acid. Aqueous silanization with 10% aminopropyltriethoxy silane coupled a layer of silane across the surface, which then formed an alkylamine substrate. The carboxyl derivative of the substrate was prepared by the reaction of the alkylamine substrate with succinic anhydride. Achromopeptidase was then coupled to the carboxy surface using carbodiimide. Albumin was similarly coupled to surfaces to serve as a control. Other substrate controls included washed substrates, alkyl amine substrates, alkyl carboxyl substrates, and carbodiimide substrates.

(c) Polymixin-B

Polymixin-B was immobilized on silicone test surfaces as described above for the enzyme achromopeptidase and on agarose beads by standard procedures.

Results

Bacterial Growth Assays

Turdidometric assays of bacterial growth were carried out with polymixin-B immobilized on a wide variety of substrates. The results showed conclusively that the immobilized antibiotic maintained activity against both *E. coli* and *S. epidermidus*. Representative results of turbidimetric assays are presented in Example IV, Table I, to provide documentation as to the inhibition of bacterial growth by immobilized antibiotics.

TABLE I

Example IV,
Turbidity Assays of Bacterial Growth Inhibition
by Immolilized Polymixin-B

| Surface | Test Organsim | Average Growth Lag (at ½ max. growth in hours) |
|---|---|---|
| Polymixin-B on Silicone | *Staphylococcus epidermidus* | 1.1 |
| Polymixin-B on Agarose Beads | *Escherichia coli* | 3–7 |
| Comparable concentration of free polymixin-B | *Escherichia coli* | 13.8 |

The effects of immobilized bioactive materials on bacterial growth were also assayed by counting the number of colony-forming units o n test and control surfaces. The results obtained when sterilized surfaces were compared is presented in Example IV, Table II.

TABLE II

Example IV
Comparison of *Staphylococcus epidermidus*
colony forming units (CFU) on sterilized
surfaces and upon Quaternary Ammonium and
Achromopeptidase Treated Surfaces
(treated prior to sterilzation)

| | Surface Treatment | | |
|---|---|---|---|
| Sterilization Method | Quaternary Untr. | Ammonium | AChr. |
| Autoclaved | 4.0 | 0 | 2.5 |
| Alcohol | 5.8 | 1.5 | 1.3 |

Dow Corning Quaternary Ammonium Chloride reduces the number of colony forming units in the bacterial growth assay by from 40% to 60% when compared to controls. Although there is variability in the assay, the number of colony forming units are significantly reduced by the Dow quaternary ammonium Compound.

Achromopeptidase surface treatment, although generally less effective than the Dow Compound, showed a reduction in CFU's from 10–50% when compared to controls. The FIGURE summarizes the results obtained when rinsed but unsterilized silicone surfaces were compared after varied surface treatments. The untreated controls gave such prolific growth that the number of colonies formed was uncountable. For calculation of % bacterial death (i.e., no colony formed on an inoculated spot), the theoretical maximum of 82 colony forming units per quadrant was used. It was remarkable that in these tests albumin appears to present an unfavorable surface for bacterial growth.

Additional tests were performed with the treated surfaces prepared in replicate appropriate for statistical analysis. A single classification Anova analysis was carried out to compare the bacterial growth on the treated and untreated silicone surfaces. The results, as shown in Example IV, Table IV, show that the Achromopeptidase significantly reduces bacterial growth, while the albumin-treated surfaces are not significantly different than the control.

TABLE III

Example IV
Inhibition of *Staphylococcus epidermidis*
Growth on Treated Silicone Surfaces.
Single Classification Anova.

| Treatment | Confidence Level | Degrees of Freedom | F-Statistic | Significant Difference |
|---|---|---|---|---|
| Achromopeptidase vs. Untreated | 95% | 34 | 6.6479 | Yes |
| Albumin vs. Untreated | 95% | 34 | 0.0062 | No |
| Achromopeptidase vs. Albumin | 95% | 46 | 6.8689 | Yes |

The antibiotic Polymyxin B was also immobilized on silicone using sequential coupling techniques. Sequential coupling (i.e., treatment with carbodiimide alone, followed by treatment with controls and Polymyxin B) reduces the likelihood of "self-coupling" crosslinking. The agar plates were incubated at 37° C. overnight to remove bubble-causing gas. Procedures for the assay were as described for the Achromopeptidase/Albumin assay in Example IV. The results, summarized in Table IV, show that Polymyxin B immobilized on silicone inhibits bacterial (*Staphylococcus epidermidis*) growth up to 68% compared to albumin where 90% survival rate was seen. Statistical analysis shows that with a 95% confidence level, there is a significant difference between albumin and Polymyxin B treatments.

TABLE IV

Example IV
Inhibition of *Staphylococcus epidermidis*
Growth on Treated Silicone Surfaces.
Single Classification Anova.

| Treatment | Confidence Level | Degrees of Freedom | F-Statistic | Significant Difference |
|---|---|---|---|---|
| Polymyxin B vs. Albumin | 95% | 3* | 4.46 | Yes |

*Represents replicates which contain 24 samples each.

Bryozoan Larval Settlement

Results of larval settlement studies are summarized in Example IV, Table V.

Dow Corning Quaternary Ammonium Chloride was ineffective in preventing settlement of bryozoan larvae. Between 90% and 100% of the larvae introduced settled in both the control and the Quaternary Ammonium Chloride treated dishes. Similarly, in the 22 hour larval barnacle settlement assay, there was not significant inhibition of barnacle settlement (control settlement 56%, DOW settlement 53%).

Two experiments were performed examining the effectiveness of Achromopeptidase in preventing settlement of bryozoan larvae. In the first experiment, Bugula settlement was quantified. Albumin was also coupled as a protein control. Additionally, representatives of these surfaces that were drained but not rinsed and other like surfaces that were rinsed 5 times with filtered sea water were compared. The surface were examined for Bugula settlement after thirty minutes and then incubated for an additional hour; the loose larvae were rinsed out of the dishes with sea water and a barnacle settlement assay performed on the dishes. As indicated in Table V, the only treatments effective against bryozoan larvae were the unrinsed coupled protein treatments. These treatments killed the larvae, indicating the presence of trace amounts of toxic compounds, presumably those used in the coupling of proteins to the surfaces. Barnacle larvae exposed to the dishes after incubation with bryozoan larvae and rinsing to remove unattached larvae survived in all cases.

TABLE V

Example IV
Settlement of Bryozoans and Barnacles

| Treatment | Bugula Settlement Percentage | Barnacle Settlement Percentage |
|---|---|---|
| Albumin (rinsed) | 100 | 27 |
| Albumin (no rinse) | 0 | 44 |
| Achromopeptidase (rinsed) | 100 | 39 |
| Achromopeptidase (no rinse) | 0 | 0 |

Example V
Properties of Paints Containing Immobilized Bioactive Materials

Background:

The polyurethane matrix can maintain a number of enzymes in an active state. This has been demonstrated for a number of the enzymes as noted in other sections of this document. In particular, we may cite maintenance of enzymatic activity for bacterial protease, trypsin, chitinase, papain, and achromopeptidase. It was desirable to document that an enzyme could maintain functional activity when mixed with a traditional paint such as a latex-based paint or an enamel (if premixed with the polyurethane prepolymer) and it was also desirable to document that smooth coatings could be made by mixing hydrophillic polyurethane prepolymers with such paints and, if desired, in combination with other appropriate bioactive materials such as surfactants.

Methods:

A non-foaming type of hydrophillic polyurethane was selected as most appropriate for generation of smooth coatings. Samples of this sort were obtained from the Grace Chemical Co. who identifies such materials as Hydrogel. The non-foaming hydrophillic polyurethane was combined to form coatings of varied sorts by hand mixing with surfactants, enzyme solutions and paints (varnish, gloss enamel that was oil-based, and satin and flat latex paints that were water-based paints).

Results:

Smooth coatings were obtained from one-to-one combinations of the polyurethane and the paints of interest (varnishes, oil- and water-based paints). Other than one-to-one combinations were found to be possible but the range of combinatorial possibilities was not systematically explored.

Surfactants (in equal volume) were found to facilitate the mixing when the paint was an oil-based paint or a varnish. When the polyurethane was not a non-foaming variety the coating obtained tended to form microbubbles. Foaming of such coatings can be manipulated by variations in mixing and/or drying procedures such as evacuation during drying or prolonged mixing.

The functionality of enzymes in the resultant coating was verified by use of an enzyme whose activity resulted in a colored product. The specific reaction catalyzed by the hydrolytic enzyme, isolated from a flavobacterium, is that shown below:

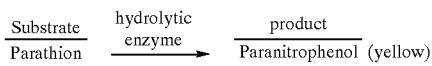

The results of tests using this enzyme in latex paints formulated as described above are summarized in Example V, Table I. Prior to assays of enzyme functionality, the coating materials were painted on glass slides, air-dried for four days and then rinsed with 5OmM Glycine-NaOH buffer, pH 9.5, five to ten times. Substrate addition was done in three increments (morning, afternoon—incubated overnight—and next morning). Buffer rinses between trials were done to remove product and any enzyme that has been released from the coating.

Example V, Table I
Enzyme Functionality in Paints Formulated with Varied Combinations of Polyurethane and Enzymes. C Designates Clear, with No Optically Detectable Product (paranitrophenol) Formation. Y Designates Optically Detectable (yellow) Product Formation.
The Table of Contents Indicate the Status of the Paint Surface and the Surrounding Solution.

| Coating | 10 minutes after 1st substrate addition Surface/-Solution | 10 minutes after 2nd substrate addition Surface/-Solution | after overnight incubation Surface/-Solution | 10 minutes after 3rd substrate addition Surface/-Solution |
|---|---|---|---|---|
| Paint + Polyurethane | C/C | — | C/C | — |
| Polyurethane + Enzyme | Y/C | — | Y/Y | — |
| Paint + Enzyme | Y/Y | Y/Y | Y/Y | C/C |
| Paint + Enzyme + Polyurethane | Y/C | Y/C | Y/Y | Y/C |
| Paint | C/C | — | C/C | — |

Conclusions:

From the results obtained, it is clear that the conventional paints can be formulated with hydrophilic polyurethanes, surfactant.s and enzymes. In the case of the specific enzyme tested, the functionality was clearly shown to persist after immobilization in the paint/polyurethane coating. It was surprising to find that simple mixing of the enzyme with the paint (without polyurethane) did not inactivate the enzyme, although there is a diminution in activity as shown by the lack of color change after the 3rd substrate addition (see Table I, above). This suggests that some of the activity observed may well have been from enzyme that was slowly released rather than truly immobilized in the formulations without polyurethane.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method for preventing fouling of an aquatic apparatus by an aquatic organism without contamination of the environment, which comprises:

applying a composition containing an inert matrix having an enzyme chemically bonded thereto, to a surface of said apparatus, wherein said chemically bonded enzyme is capable of hindering attachment of said organism to said surface while applied to said surface; and contacting at least part of said surface with an aquatic environment which contains an aquatic organism capable of fouling said aquatic apparatus and is one aquatic environment selected from the group consisting of natural fresh-water environments, estuary aquatic environments, sea waters, cooling tower systems, fresh water piping systems, salt water piping systems, ponds, lakes, harbors, dredged channels, and desalination systems, thereby hindering attachment of said organism to said surface by interfering with said organisms mechanisms for attachment to submerged surfaces.

2. The method of claim 1 wherein said surface is non-porous.

3. The method of claim 1 wherein said surface is smooth.

4. The method of claim 1 wherein said surface is an external surface of an aquatic apparatus.

5. The method of claim 1 wherein said aquatic environment is one aquatic environment selected from the group consisting of sea waters, cooling tower systems, fresh water piping systems, salt water piping systems, desalination systems, ponds, lakes, and dredged channels.

6. The method of claim 1 wherein said enzyme is a serine protease, a sulfhydryl protease, or a metalloprotease.

7. The method of claim 1 wherein said organism is a bacterium, fungus, alga, protozoan, poriferum, coelenterate, platyheminthe, neinerta, rotifera, bryozoan, brachiopod, annelid, arthropod, mollusc, chordate, or echinodermate.

8. The method of claim 1 wherein said organism is a unicellular organism.

9. The method of claim 1 wherein said enzyme is chitinase, papaya protease, Streptomyces protease, β-amylase, β-glucosidase, glycosidase, cellulase, pectinase, collagenase, hyaluronidase, β-glucuronidase, trypsin, chymotrypsin, subtilisin, chymopapain, carboxpeptidase A or B, or thermolysin.

10. The method of claim 1, wherein said aquatic apparatus is one member selected from the group consisting of ship hulls, pilings, glass and other transparent observation windows, sonar domes, water-conducting pipes, cooling towers, ponds, pumps, valves, and filtration members.

11. The method of claim 1, wherein said aquatic environment is an estuary, or a harbor.

12. The method of claim 1, wherein said organism is a plant or an animal.

13. The method of claim 1, wherein said organism is at least one member selected from the group consisting of bacteria, fungi, algae, protozoa, porifera, coelenterata, platyhelminthes, nemertea, rotifera, bryozoa, brachiopoda, annelida, arthropoda, mollusca, echinodermata, and chordata.

14. A method for preventing fouling of an aquatic apparatus by an aquatic organism without contamination of the environment, which comprises:

coating a surface of said apparatus with a composition containing an inert matrix and a biologically active enzyme chemically bonded to said inert matrix, wherein said enzyme is capable of hindering attachment of said organism to said surface while coated on said surface, wherein said apparatus is one member selected from the group consisting of ship hulls, pilings, glass and other transparent observation windows, sonar domes, water-conducting pipes, cooling towers, ponds, pumps, and valves.

* * * * *